US012508131B2

(12) United States Patent
Carr et al.

(10) Patent No.: US 12,508,131 B2
(45) Date of Patent: Dec. 30, 2025

(54) INSERT FOR USE IN A KNEE PROSTHESIS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Christopher B. Carr, Bartlett, TN (US); Nathaniel M. Lenz, Germantown, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 481 days.

(21) Appl. No.: 18/020,570

(22) PCT Filed: Sep. 22, 2021

(86) PCT No.: PCT/US2021/051423

§ 371 (c)(1),
(2) Date: Feb. 9, 2023

(87) PCT Pub. No.: WO2022/066688

PCT Pub. Date: Mar. 31, 2022

(65) Prior Publication Data

US 2023/0310165 A1 Oct. 5, 2023

Related U.S. Application Data

(60) Provisional application No. 63/082,759, filed on Sep. 24, 2020.

(51) Int. Cl.
*A61F 2/38* (2006.01)

(52) U.S. Cl.
CPC .......... *A61F 2/3886* (2013.01); *A61F 2/3859* (2013.01); *A61F 2/389* (2013.01)

(58) Field of Classification Search
CPC ...... A61F 2/389; A61F 2/3886; A61F 2/3868; A61F 2002/30934
See application file for complete search history.

(56) References Cited

U.S. PATENT DOCUMENTS 7,066,963 B2 6/2006 Naegerl
7,922,771 B2 4/2011 Otto
(Continued)

FOREIGN PATENT DOCUMENTS

WO 2007108804 A1 9/2007
WO 2010151564 A1 12/2010
(Continued)

OTHER PUBLICATIONS

International Search Report and Written Opinion for the International Patent Application No. PCT/US2021/051423, mailed Jan. 5, 2022, 14 pages.
(Continued)

*Primary Examiner* — Javier G Blanco
(74) *Attorney, Agent, or Firm* — KDW Firm PLLC

(57) ABSTRACT

An insert for use in a knee prosthesis is disclosed. In one embodiment, the insert includes a medial compartment and a lateral compartment. The medial compartment includes a top surface having a concave surface or curve with a more posterior sulcus and increased anterior lip. The lateral compartment includes a top surface having at least a segment or portion with a convex surface or curve. Thus arranged, the insert is arranged and configured to provide improved stability for varying grades of PCL deficiencies compared to existing inserts that have a mid-line sulcus and lateral convexity. In addition, the insert provides improved lateral
(Continued)

posterior translation compared to existing designs with a concave or flat lateral articulation that lack a lateral posterior convexity.

10 Claims, 17 Drawing Sheets

(56) References Cited

U.S. PATENT DOCUMENTS

| | | | |
|---|---|---|---|
| 9,642,711 | B2 | 5/2017 | Carson |
| 10,149,768 | B2 | 12/2018 | Otto |
| 10,278,827 | B2 | 5/2019 | Drury |
| 10,893,946 | B2 | 1/2021 | Sun |
| 2008/0161918 | A1 | 7/2008 | Fankhauser |
| 2010/0036499 | A1 | 2/2010 | Pinskerova |
| 2019/0209331 | A1 | 7/2019 | Varadarajan |

FOREIGN PATENT DOCUMENTS

| | | | |
|---|---|---|---|
| WO | 2013009966 | A2 | 1/2013 |
| WO | 2017117337 | A1 | 7/2017 |

OTHER PUBLICATIONS

Smith & Nephew—Journey™ II CR Total Knee System—Surgical Technique Brochure—2019, 60 pages.

INSERT FOR USE IN A KNEE PROSTHESIS

CROSS-REFERENCE TO RELATED APPLICATIONS

This application is a National Phase filing of International Application No. PCT/US2021/051423, filed Sep. 22, 2021, which application is a non-provisional of, and claims the benefit of the filing date of, U.S. provisional patent application No. 63/082,759, filed Sep. 24, 2020, entitled "Insert for Use in a Knee Prosthesis," the entirety of each application is incorporated by reference herein.

FIELD OF THE DISCLOSURE

The present disclosure is directed to an orthopedic implant, and more particularly to an insert for use in an orthopedic knee prosthesis.

BACKGROUND

Knee arthroplasty or knee replacement procedures generally involve the implantation, installation, etc. (used interchangeably herein without the intent to limit) of an orthopedic implant such as a knee prosthesis onto a patient's knee. For example, in connection with a total knee arthroplasty or knee replacement ("TKA"), the orthopedic implant (e.g., knee prosthesis) may include a femoral component and a tibial component. In use, the femoral component is attached to the patient's femur while the tibial component is attached to the patient's tibia. Generally speaking, the femoral and tibial components may each include a support member such as, for example, an intramedullary stem, which is attachable to an articular component, a tray, a load bearing component, etc. (terms used interchangeably herein without the intent to limit). In use, the support member is arranged and configured to be coupled to the patient's bone and may be, for example, inserted within an intramedullary canal of the patient's bone while the tray mounts upon a prepared surface on the patient's bone. A bearing member or insert is typically mounted upon the tray of the tibial component.

TKA may be performed to address damage within multiple compartments of the patient's knee joint due to, for example, arthritis. The TKA procedure aims to alleviate chronic pain within the joint and restore function to the disabled knee. Early knee prosthesis tended to focus primarily on stabilizing the knee through guided motion while mostly ignoring the patient's native ligament structures. However, with the advancement in joint replacement surgery and improvements with implant fixation, new designs have emerged that work in conjunction with the patient's soft tissue structures, enabling increased kinematic freedom of the patient's femur relative to the patient's tibia while providing varying degrees of stability based on the patient's specific needs and surgeon preferences.

Today, knee prosthesis can be grouped into four main classification types based on how the cruciate ligaments are managed. Posterior stabilized ("PS") designs sacrifice both cruciate ligaments of the patient's knee while substituting for the posterior cruciate ligament ("PCL") by way of a cam and post mechanism which helps to control anterior translation during knee flexion. Cruciate-sacrificing ("CS") and Deep Dish ("DD") designs also allow for resection of both cruciate ligaments while offering more conforming articular geometries to help stabilize the joint. Cruciate-retaining ("CR") designs sacrifice only the anterior cruciate ligament while preserving the PCL with the intent that this structure will provide anterior/posterior (A/P) stability for the femur as it flexes relative to the tibia while the less conforming articular geometries enable for increased autonomous motion. The fourth type of TKA is the bi-cruciate retaining ("BCR") design which preserves both cruciate ligaments and offers limited conformity and geometrical constraint, relying solely on the soft tissue structures to drive kinematics of the knee. While BCR knee prosthesis may offer theoretical advantages for enabling more normal kinematics, the use of BCR knee prosthesis is still fairly limited as many surgeons have not adopted the more advanced surgical techniques required to perform such surgeries. As a result, the majority of TKA procedures being performed today continue to use either a PS or CR knee prosthesis design.

While PS designs tend to promote more reliable kinematics compared to most CR designs, a growing trend to preserve patient's native bone by not having to resect for the box geometry of the PS femoral component is emerging. As such, an increased number of surgeons are seeking implants like the CR and CS designs that enable for bone preservation while still providing adequate A/P constraint with reliable kinematics. In addition, surgeons who may commonly perform TKA using CR type implants may experience instances where the retained PCL does not provide acceptable A/P constraint when using many of the more standard articular CR inserts. This may be evident at the time of surgery if the PCL is found to be non-pristine or may occur post-operatively as the PCL begins to loosen and impart laxity within the joint. On the other hand, the option for using CS and DD inserts is not as desirable for use unless the patient requires additional constraint as the more conforming articular geometries may prohibit condylar motion which encourages kinematics for improved flexion of the knee.

Currently, the use of CR and CS/DD knee prosthesis by surgeons who typically perform TKA procedures using PS implants is increasing. This shift in surgical philosophy is supported by the number of CR/CS and DD type knee prosthesis, which currently exist on the market and fulfill the need for bone preservation as well as providing for increased stability even in cases when both cruciate ligaments are resected. These implant systems promote the use of specialized articular inserts with varying articular conformities and features. One existing design is a medial pivoting type knee which utilizes a trough within the medial compartment of the articular insert that closely conforms to the geometry of the medial femoral condyle. This geometry helps to prevent anterior sliding of the femur on the tibia. Other existing designs implement concave or cupped geometries within both the medial and lateral compartments of the articular insert. These options also tend to be more conforming, matching both the medial and lateral femoral condyles at defined flexion angles to promote increased A/P stability.

Nonetheless, it would be beneficial to provide an articular insert for a CR knee prosthesis that provides suitable A/P constraint with regards to the condition of the remaining native soft tissue structures while enabling for reliable kinematics that encourage improved function of the knee.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, an insert suitable for use in a knee prosthesis is disclosed. In one embodiment, the articular insert is arranged and configured to be used in connection with an existing knee prosthesis such as, for example, an existing TKA CR femoral component, which in combination with soft tissue structures, provides improved stability over existing CR insert designs while encouraging kinematics within the lateral compartment which help to promote improved rotational movement and flexion of the knee compared with existing CS/DD insert designs.

In one embodiment, the insert includes a generally concave medial compartment and a convex lateral compartment. That is, in one embodiment, the insert includes a medial compartment for contacting with a medial condylar surface formed on the femoral component or bone and a lateral compartment for contacting a lateral condylar surface on the femoral component or bone. The medial compartment includes a top surface having a generally concave surface or curve. The lateral compartment includes a top surface having a compound curve having at least a portion or segment that includes a generally convex surface or curve.

Thus arranged, in use, the medial sulcus for the articular insert is positioned substantially more posterior, allowing for an increased anterior lip with a fully concave geometry closely matching that of the femoral component's medial femoral condyle in the region of contact for compatible sized femurs. As a result, the medial compartment is able to provide sufficient medial constraint for both PCL deficient and sacrificed conditions. In conjunction with a concave medial compartment providing added stability, the lateral compartment is optimized to have an anterior concavity with a relaxed anterior lip to enable for screw-home during extension. This lateral anterior concavity transitions to a reversely contoured convexity having increased slope along the posterior half of the articular surface to promote lateral posterior translation while helping to impart external rotation of the femur with respect to the tibia as the knee moves into deeper flexion.

In one embodiment, an insert suitable for use in a knee prosthesis including a femoral component and a tibial component is disclosed. The insert includes an anterior surface, a posterior surface, a medial surface, a lateral surface, a top surface, a bottom surface, a medial compartment, and a lateral compartment. In use, the medial compartment is arranged and configured to interact with a medial condylar surface of a femoral component. The lateral compartment is arranged and configured to interact with a lateral condylar surface of the femoral component. In one embodiment, the medial compartment includes a concave top surface for contacting the medial condylar surface of the femoral component while the lateral compartment includes a top surface including a compound curve having at least a convex top segment for contacting the lateral condylar surface of the femoral component.

In one embodiment, the concave top surface of the medial compartment includes a medial sulcus point, the medial sulcus point being positioned closer to the posterior surface than to the anterior surface.

In one embodiment, the medial sulcus point is positioned a distance D from the posterior surface of the insert, wherein distance D is approximately 35% to 40% of an overall distance between the posterior and anterior surfaces of the insert.

In one embodiment, the anterior surface includes an anterior lip having a height $H_A$ as measured from the medial sulcus point to a tip of the anterior lip and a posterior lip having a height $H_p$ as measured from the medial sulcus point to a tip of the posterior lip, where height $H_A$ is greater than height $H_p$.

In one embodiment, the height $H_A$ at the anterior lip is between 6.5 mm and 10 mm.

In one embodiment, the height $H_p$ at the posterior lip is between 3 mm and 4 mm.

In one embodiment, the concave top surface extends completely from the posterior surface to the anterior surface.

In one embodiment, the compound top surface of the lateral compartment includes an anterior concavity (e.g., an anterior segment including a concave surface) that transitions to a reversely contoured convexity (e.g., to the convex segment).

In one embodiment, the compound top surface includes a concave posterior segment positioned between the posterior surface of the insert and the convex top segment.

In one embodiment, the compound top surface includes a posterior concave intermediate segment positioned between the concave posterior segment and the convex top segment.

In one embodiment, the compound top surface includes an anterior concave segment positioned between the anterior surface of the insert and the convex top segment.

In one embodiment, the compound top surface includes a flat segment positioned between the anterior concave segment and the convex top segment.

In one embodiment, the compound top surface of the lateral compartment includes a lateral sulcus point defined as a transition between the anterior concave segment and the flat segment (e.g., the lateral sulcus point resides at the transition between the anterior concave segment and the flat segment).

In one embodiment, the compound top surface of the lateral compartment includes a lateral sulcus point at the most posterior end of the anterior concave segment (e.g., the lateral sulcus point resides at a posterior end of the anterior concave segment).

In one embodiment, the lateral sulcus point is positioned a distance D from the posterior surface of the insert, the lateral sulcus point being positioned closer to the anterior surface of the insert than to the posterior surface.

In one embodiment, the distance D from the posterior surface of the insert is 50% to 65% of an overall distance between the posterior and anterior surfaces of the insert.

In one embodiment, the top surface of the medial component includes a medial sulcus point and the top surface of the lateral component includes a lateral sulcus point, wherein the lateral sulcus point is positioned closer to the anterior surface of the insert than the medial sulcus point (e.g., the medial sulcus point is positioned closer to the posterior surface of the insert than the lateral sulcus point).

In one embodiment, the compound top surface of the lateral compartment includes a transition point defined as point of transition to the posterior convexity (e.g., point of transition between the flat segment and the convex top segment).

In one embodiment, the compound top surface of the lateral compartment includes a transition point defined as anterior start of the convex top segment (e.g., the transition point resides at an anterior end of the convex segment).

In one embodiment, the transition point is positioned a distance T from the posterior surface of the insert with distance T being approximately 40% to 50% an overall distance between the posterior and anterior surfaces of the insert.

In one embodiment, the anterior surface of the lateral compartment includes an anterior lip having a height $H_A$ and a posterior lip having a height $H_p$, where height $H_A$ is greater than height $H_p$.

In one embodiment, the insert is arranged and configured to be used in a knee prosthesis in a surgical procedure where a patient's posterior cruciate ligament is retained and in a surgical procedure where a patient's posterior cruciate ligament is resected.

In an alternate embodiment, a knee prosthesis is disclosed. The knee prosthesis including a femoral component, a tibial component, and an insert. The femoral component includes a medial condylar surface, a lateral condylar surface, and an articular surface. The tibial component includes a load bearing component. The insert is positioned between the articular surface and the load bearing component, the insert including an anterior surface, a posterior surface, a medial surface, a lateral surface, a medial component, and a lateral component. The medial component includes a top surface arranged and configured to contact the medial condylar surface, the top surface of the medial component including a medial sulcus point. The lateral component includes a top surface arranged and configured to contact the lateral condylar surface, the top surface of the lateral component including a lateral sulcus point. The medial sulcus point is positioned closer to the posterior surface of the insert than the lateral sulcus point.

Embodiments of the present disclosure provide numerous advantages. For example, in accordance with the present disclosure, the articular insert equips surgeons choosing to perform a cruciate-retaining or cruciate-substituting TKA procedure with an option for improved adaptation to the needs of the patient and the varying soft tissue conditions which can impact knee replacement function and long-term clinical success. In accordance with one or more features of the present disclosure, the insert provides a concave medial compartment or surface with a more posterior sulcus and increased anterior lip, thereby providing improved stability for varying grades of PCL deficiencies compared to existing inserts that have a mid-line sulcus and lateral convexity. In addition, the insert provides improved lateral posterior translation compared to existing designs with a concave or flat lateral articulation that lack a lateral posterior convexity.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
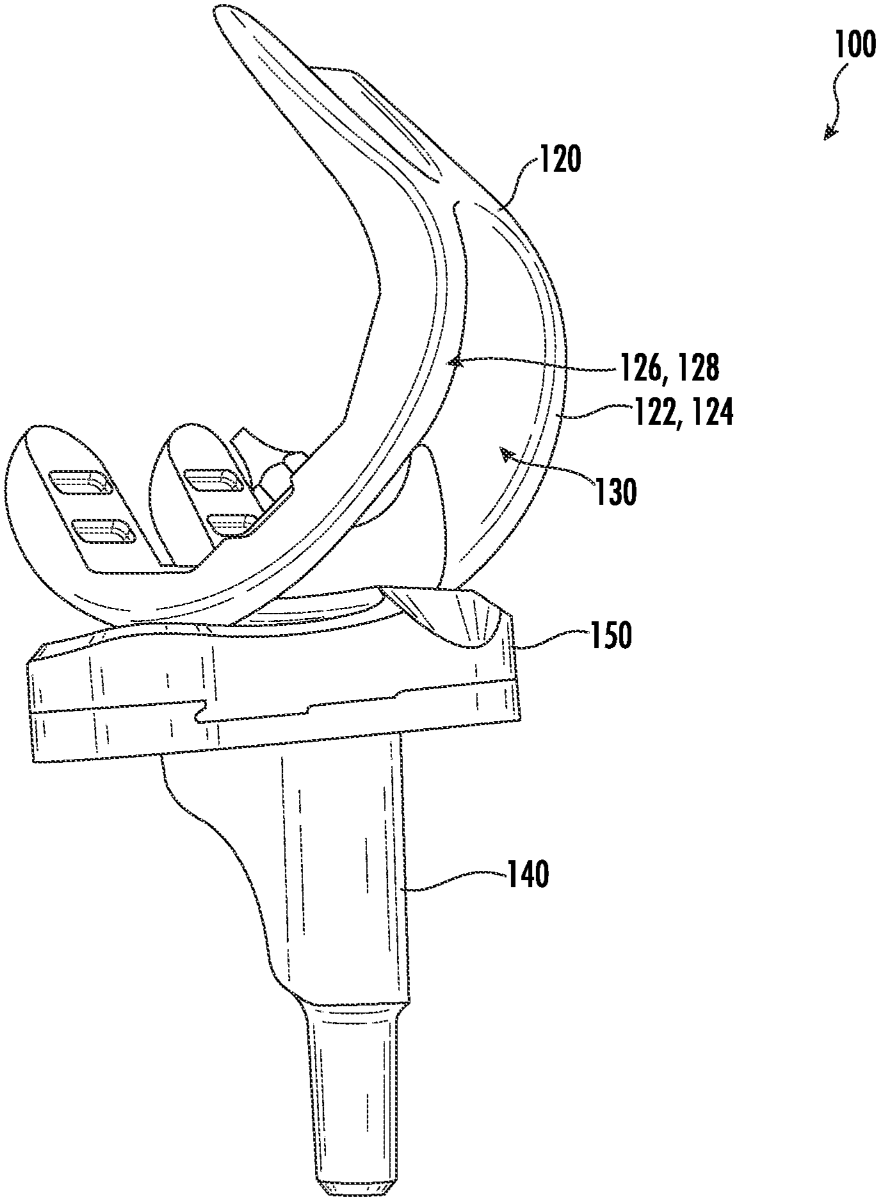
FIG. 1 is a perspective view of an embodiment of a knee prosthesis.
Figure 2:
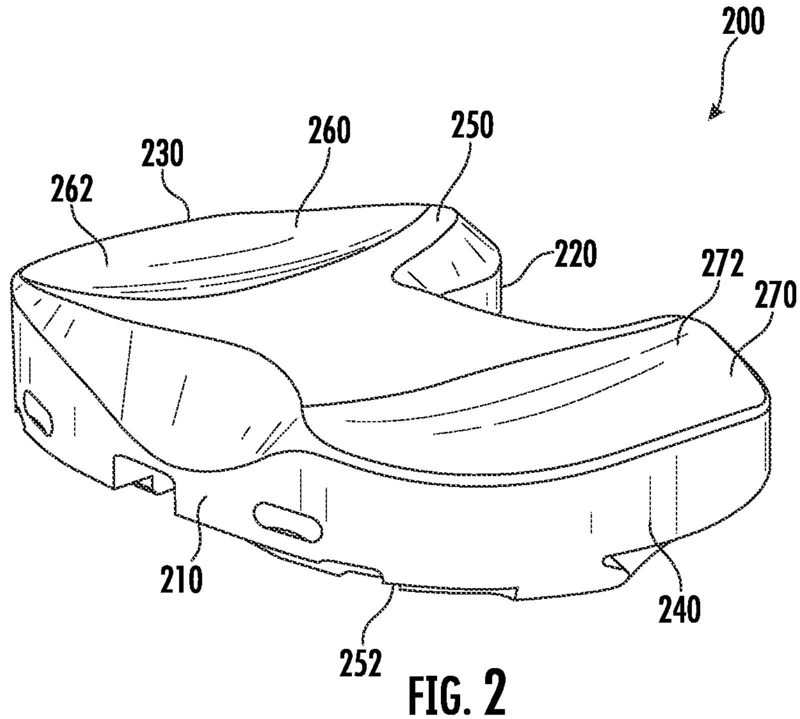
FIG. 2 is an anterior perspective view of an embodiment of an insert that may be used in the knee prosthesis shown in FIG. 1 in accordance with one or more features of the present disclosure.
Figure 3:
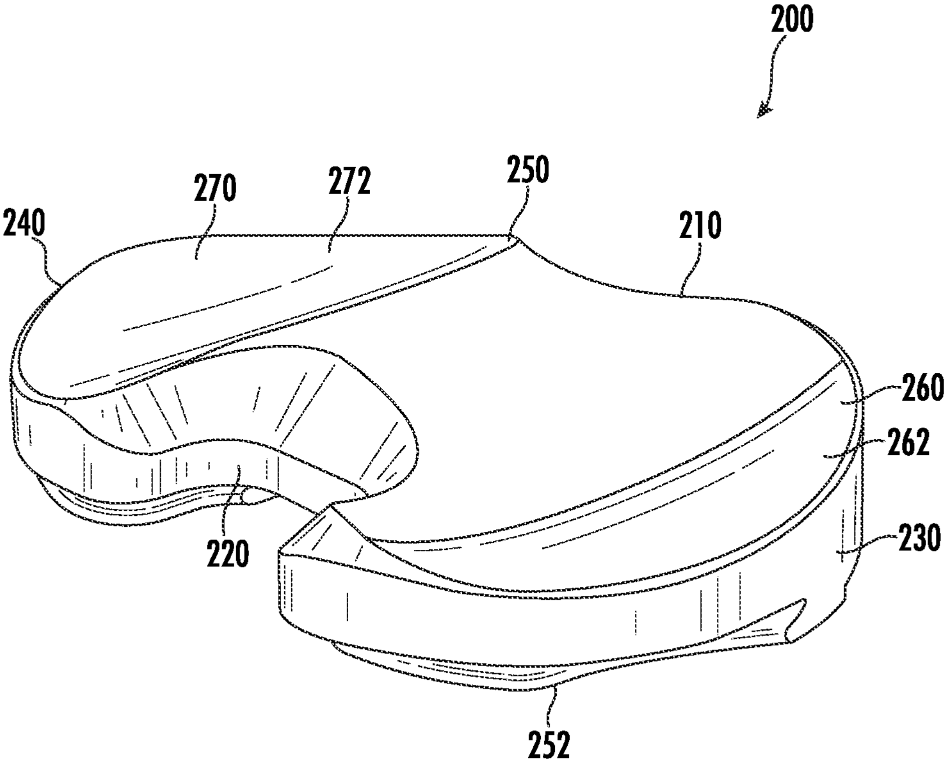
FIG. 3 is a posterior perspective view of the insert shown in FIG. 2.
Figure 4:
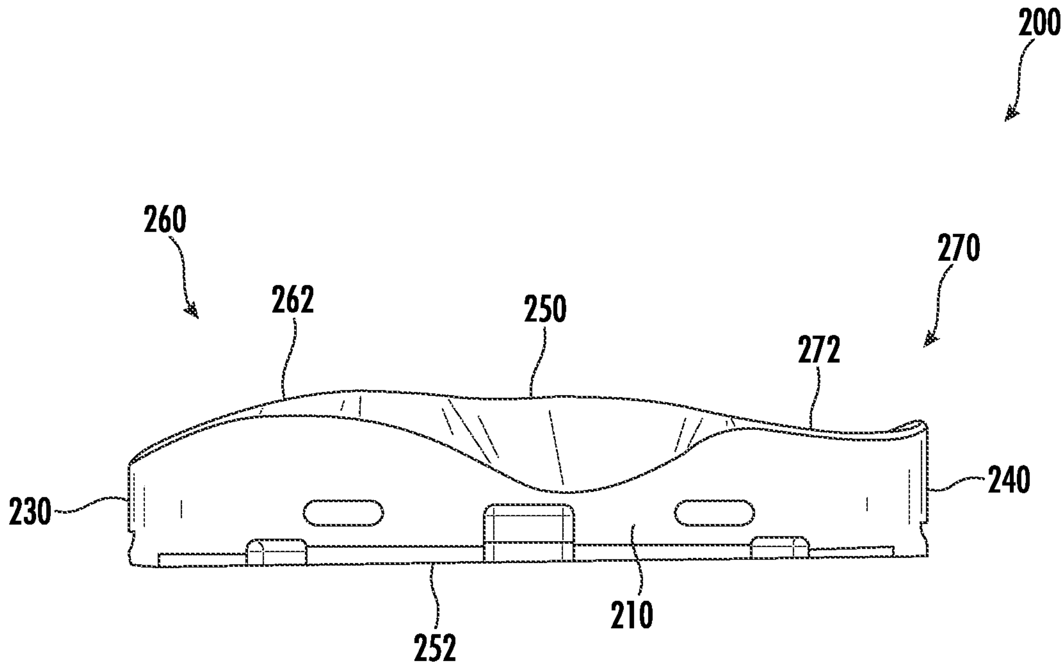
FIG. 4 is an anterior elevational view of the insert shown in FIG. 2.
Figure 5:
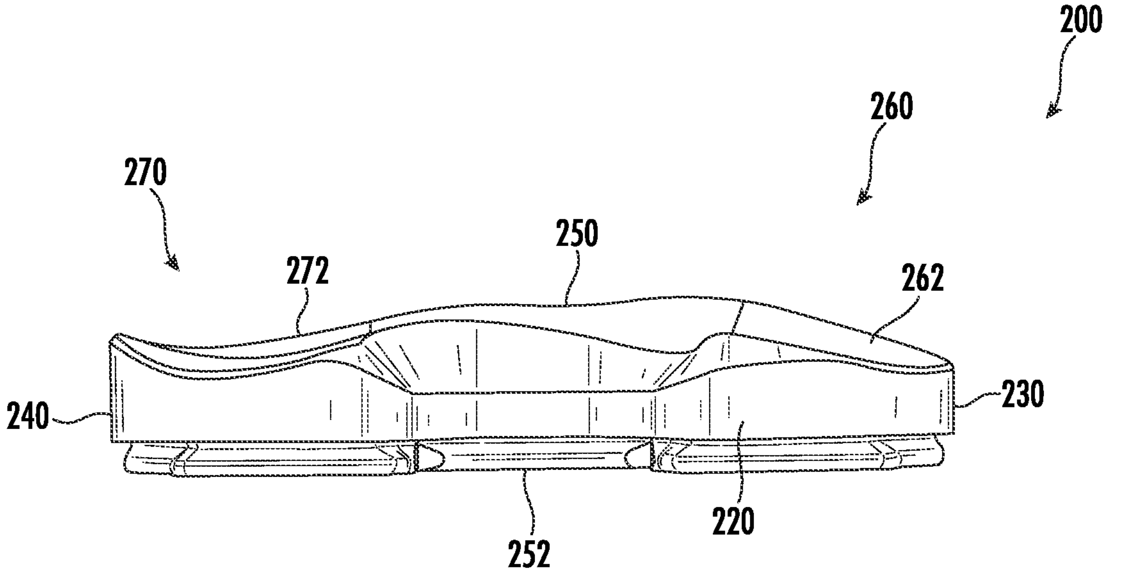
FIG. 5 is a posterior elevational view of the insert shown in FIG. 2.
Figure 6:
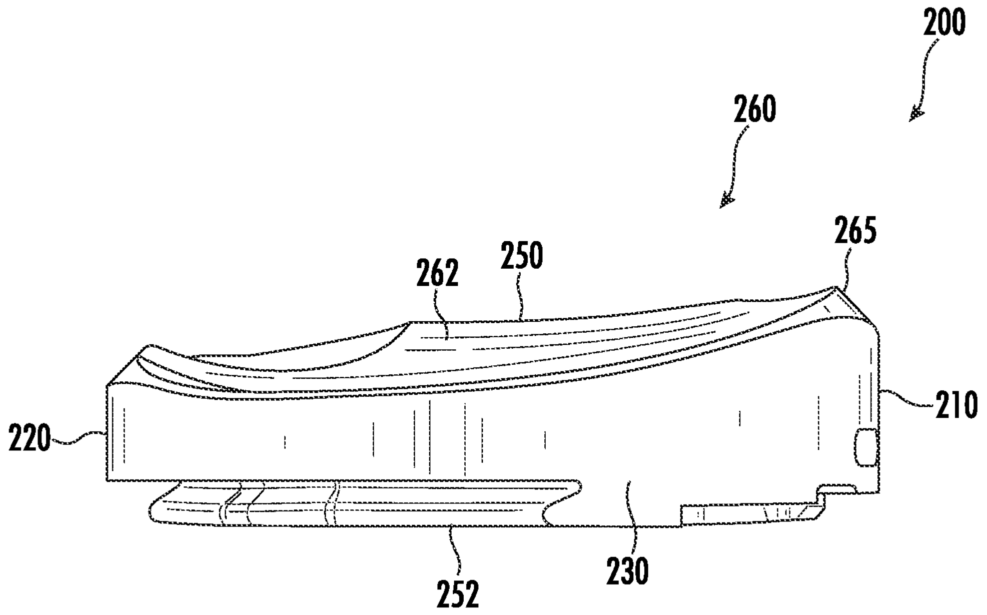
FIG. 6 is a medial side view of the insert shown in FIG. 2.
Figure 7:
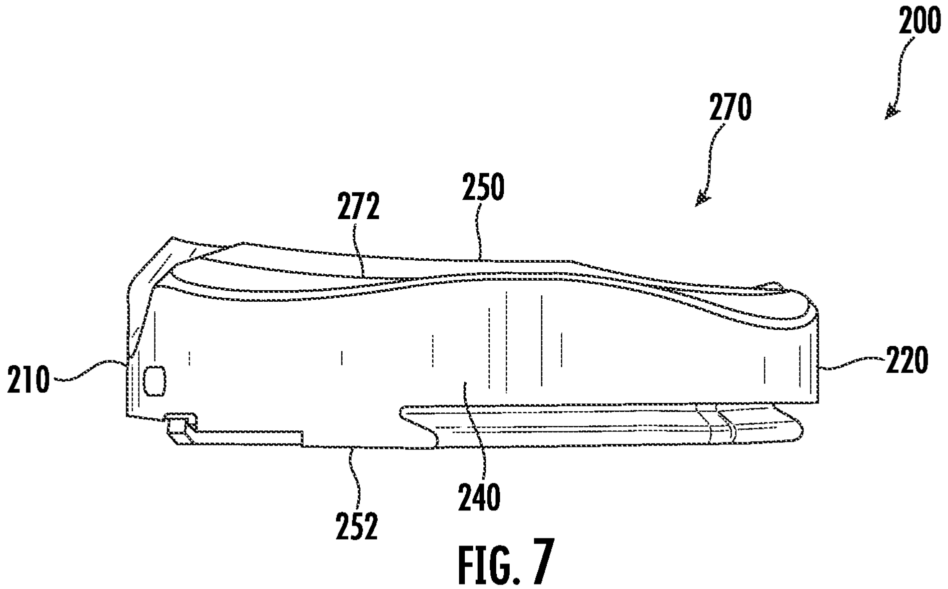
FIG. 7 is a lateral side view of the insert shown in FIG. 2.
Figure 8:
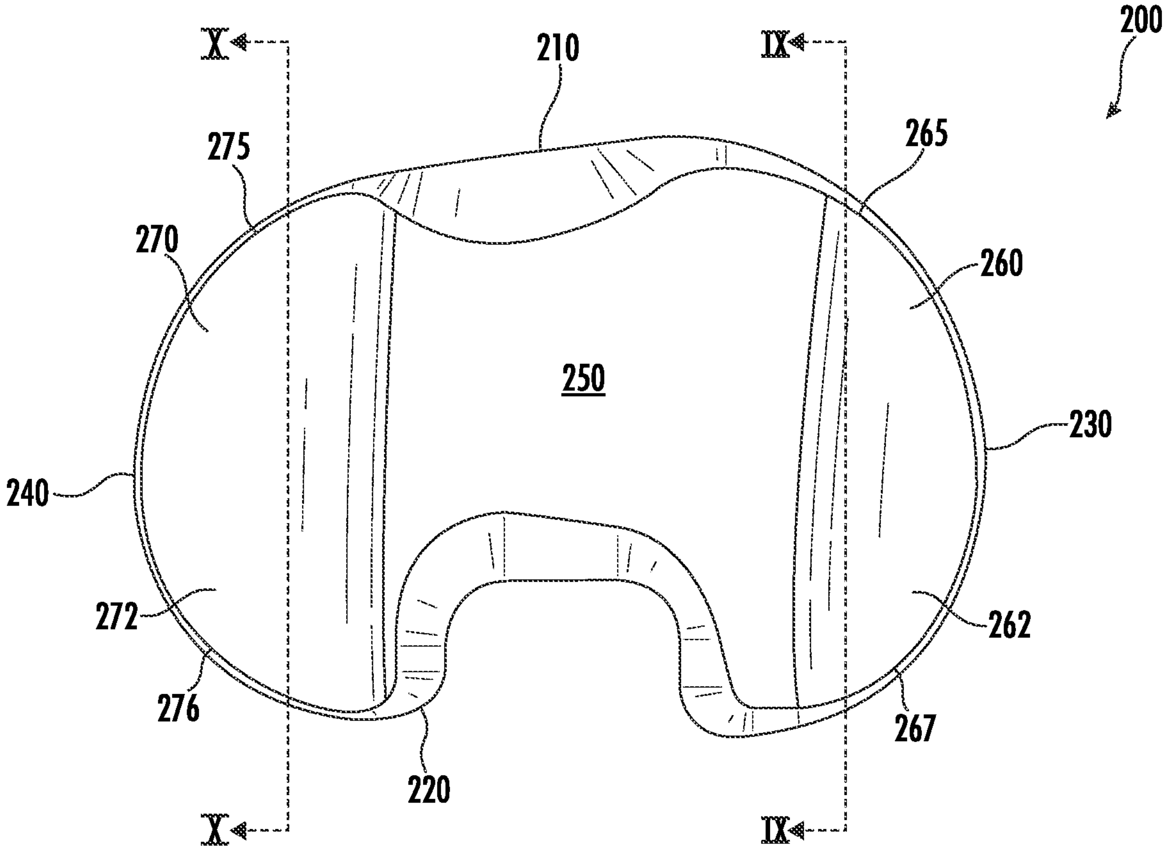
FIG. 8 is a top view of the insert shown in FIG. 2.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

DETAILED DESCRIPTION

Various features or the like of an insert arranged and configured for use in a knee prosthesis will now be described more fully hereinafter with reference to the accompanying drawings, in which one or more features of the insert will be shown and described. It should be appreciated that the various features may be used independently of, or in combination, with each other. It will be appreciated that an insert and accompanying knee prosthesis as disclosed herein may be embodied in many different forms and should not be construed as being limited to the embodiments set forth herein. Rather, these embodiments are provided so that this disclosure will convey certain features of the insert and accompanying knee prosthesis to those skilled in the art.

As will be described herein, in accordance with one or more features of the present disclosure, an insert arranged and configured for use in a knee prosthesis or implant (used interchangeably herein without the intent to limit) is disclosed. In one embodiment, as will be appreciated by one of ordinary skill, the knee prosthesis includes a tibial implant, component, etc. (used interchangeably herein without the intent to limit) and a femoral component. The tibial component generally includes a tibial tray or load bearing component (terms used interchangeably herein without the intent to limit) and a support member arranged and configured to couple to a patient's bone such as, for example, the patient's tibia. Similarly, the femoral component generally includes an articulating component and a support member arranged and configured to couple to a patient's bone such as, for example, the patient's femur. In use, the tibial tray is arranged and configured to receive the insert while the articulating component of the femoral component is arranged and configured to move (e.g., articulate) against a top surface of the insert.

Referring to FIG. 1, a knee prosthesis 100 includes a femoral component 120 and a tibial component 140. During use, as will be readily appreciated by one of ordinary skill in the art, the femoral component 120 is coupled to a distal end of a patient's femur while the tibial component 140 is coupled to a proximal end of a patient's tibia. In use, the femoral component 120 moves relative to the tibial component 140. To facilitate this movement, the knee prosthesis 100 includes an insert 150 positioned between the femoral component 120 and the tibial component 140.

Generally speaking, the insert 150 is coupled to the tibial component 140 by any suitable mechanism now known or hereafter developed such as, for example, a mechanical connection (e.g., dovetail connection), adhesive, etc. During use, the insert 150 is arranged and configured to enable the femoral component 120 to move relative to the tibial component 140. For example, the insert 150 may enable rotation of the femoral component 120 relative to the tibial component 140. In addition, the insert 150 may enable anterior-posterior translation of the femoral component 120 relative to the tibial component 140 and internal and external rotation. In use, the insert 150 may be arranged and configured to guide, control, constrain, etc. movement of the femoral component 120 relative to the tibial component 140. That is, the top surface of the insert 150 provides a surface against which the articulating condylar portions of the femoral component articulate, e.g., move in motion generally corresponding to the motion of the femur relative to the tibia.

That is, as illustrated, the femoral component 120 includes a medial condylar portion 122 with a medial condylar surface 124 and a lateral condylar portion 126 with a lateral condylar surface 128. The medial condylar surface 124 and the lateral condylar surface 128 may be rounded, and in some implementations, may be asymmetrical. Between the medial condylar surface 124 and the lateral condylar surface 128, the femoral component 120 defines a trochlear groove 130 over which a patella or a patellar implant can glide during flexion of the knee. In use, the insert includes a top surface having a medial compartment and a lateral compartment, the medial condylar surface 124 of the femoral compartment 120 is arranged and configured to contact to the top surface of the medial compartment while the lateral condylar surface 128 of the femoral compartment 120 is arranged and configured to contact to the top surface of the lateral compartment.

Referring to FIGS. 2-10, in accordance with one or more features of the present disclosure, an improved insert 200 that may be used in a knee prosthesis is illustrated. In use, the insert 200 may be used in the knee prosthesis 100 shown and described in connection with FIG. 1 in place of insert 150. However, it should be appreciated that the insert 200 may be used in connection with other suitable knee prosthesis now known or hereafter developed. As such, it should be understood that the insert of the present disclosure is not limited to any particular knee prosthesis.

The insert 200 may have any suitable shape now known or hereafter developed. For example, the insert 200 may have any shape sized and configured to correspond to a shape of the femoral and tibial components. As shown and described the insert 200 may be sized and configured as a full insert sized and configured for use in a total knee replacement surgery or revision knee replacement surgery. In one embodiment, the insert may be manufactured as a monolithic or unitary member. Alternatively, it is envisioned that the insert may be manufactured from multiple parts that are then coupled together. For example, in one embodiment, the insert may comprise lateral and medial components representing the medial and lateral compartments individually, the lateral and medial compartments being coupled together by any suitable mechanism or method now known or hereafter developed such as, for example, via an adhesive, mechanical connection, mechanical fasteners, etc.

In addition, the insert 200 may include a notch formed in a posterior surface thereof. In one embodiment, the insert 200 may be sized and shaped to match an outer profile of the femoral and/or tibial components although such is not necessary. In addition, and/or alternatively, the insert may be arranged and configured to couple to the tibial and/or femoral component by any suitable mechanism now known or hereafter developed. The insert may be manufactured from any suitable material now known or hereafter developed.

As illustrated, in one embodiment, the insert 200 may be arranged and configured for use in a left knee prosthesis. However, as will be appreciated by one of ordinary skill in the art, the insert 200 may be arranged and configured for use in a right knee prosthesis, the insert for a right knee prosthesis being a mirror image of the insert for the left knee prosthesis. In either event, the insert 200 includes an anterior surface 210, a posterior surface 220, a medial surface 230, a lateral surface 240, a top surface 250 and a bottom surface 252.

In one embodiment, the bottom surface 252 of the insert 200 is arranged and configured to couple to the tibial component such as, for example, tibial component 140. In one embodiment, the insert 200 may be coupled to the tibial component by a mechanical connection such as, for example, a dovetail connection, interlocking projections and recesses, etc., although other suitable connection mechanisms may be used.

As illustrated, the top surface 250 of the insert 200 includes a medial compartment 260 and a lateral compartment 270. In use, the medial compartment 260 is arranged and configured to interact with the medial condylar surface 124 of the femoral component 120 and the lateral compartment 270 is arranged and configured to interact with the lateral condylar surface 128 of the femoral component 120. In accordance with one or more features of the present disclosure, the medial compartment 260 includes a generally concave top surface 262 for contacting the medial condylar surface 124 of the femoral component 120 of a knee prosthesis while the lateral compartment 270 includes at least a portion of a convex top surface 272 for contacting the lateral condylar surface 128 of the femoral component 120 of the knee prosthesis. Thus arranged, by providing a generally concave top surface 262 in the medial compartment 260 of the insert 200, the medial sulcus for the articular insert 200 is positioned more posteriorly towards the posterior surface 220 of the insert 200 as compared to existing inserts incorporating a convex lateral articular surface (e.g., referring to FIG. 9, as will be described in greater detail herein, the medial sulcus coincides with the lowest point on the concave top surface 262 and is positioned a distance D from the posterior surface 220 of the insert 200). In addition, and/or alternatively, by providing a generally concave top surface 262 in the medial compartment 260 of the insert 200, the anterior lip 265 of the insert 200 may be increased (e.g., the height of the anterior lip 265 of the insert 200 in the medial compartment 260 of the insert 200 is increased compared to existing inserts). Thus arranged, by providing an increased anterior lip 265 with a fully concave top surface 262 enables the medial compartment 260 to provide sufficient medial constraint for both PCL deficient and sacrificed conditions.

Figure 10:
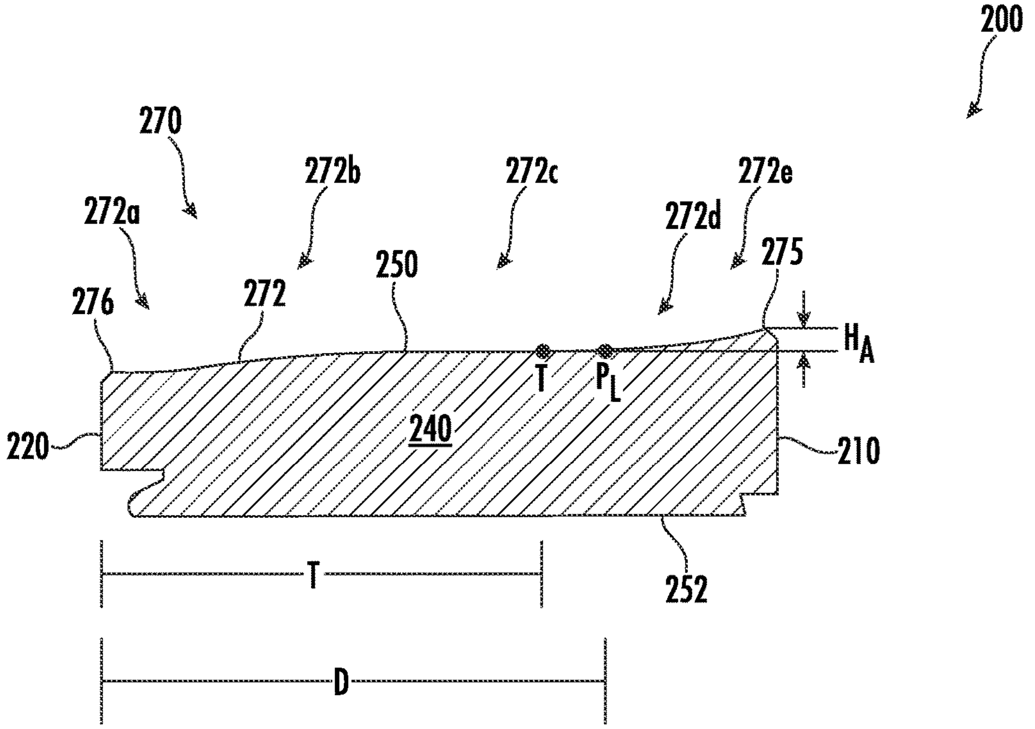
FIG. 10 is a cross-sectional view of the insert shown in FIG. 2, the cross-sectional view taken through the lateral articular surface of the insert along line X-X in FIG. 8 (i.e., the cross-sectional view taken along a designed contact path on the lateral side measuring 24 mm from a midline of the insert)
Figure 11:
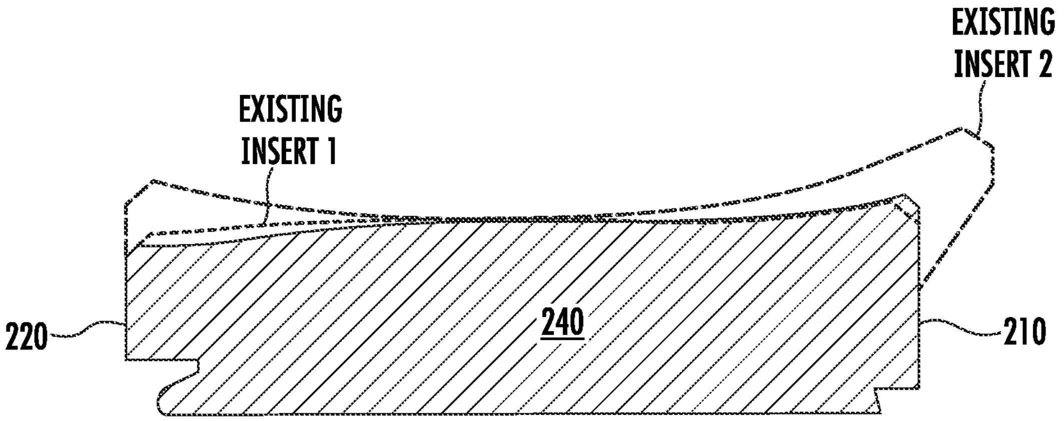
FIG. 11 is a schematic view of the insert shown in FIG. 2 illustrating the cross-sectional geometry taken through the lateral articular surface of the insert as compared to known existing inserts (existing Insert 1 and existing Insert 2)
Figure 12:
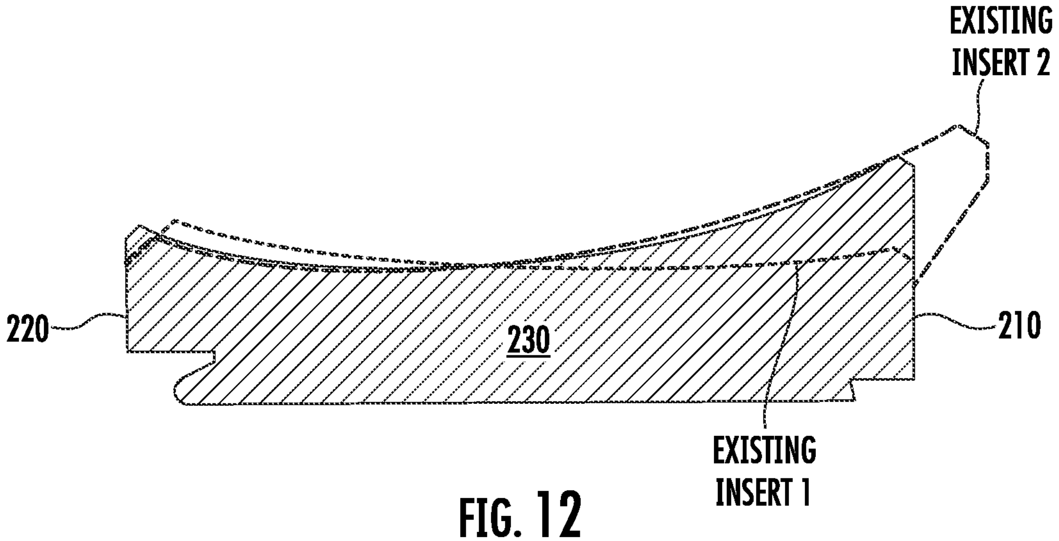
FIG. 12 is a schematic view of the insert shown in FIG. 2 illustrating the cross-sectional geometry taken through the medial articular surface of the insert as compared to the known existing inserts (e.g., existing Insert 1 and existing Insert 2)

Referring to FIG. 10, the lateral compartment 270 may be arranged and configured to incorporate an anterior concavity with a relaxed anterior lip to enable for screw-home during extension. As illustrated, the lateral anterior concavity transitions to a reversely contoured convexity having increased slope along the posterior half of the articular surface to promote lateral posterior translation while helping to impart external rotation of the femur with respect to the tibia as the knee moves into deeper flexion.

Figure 9:
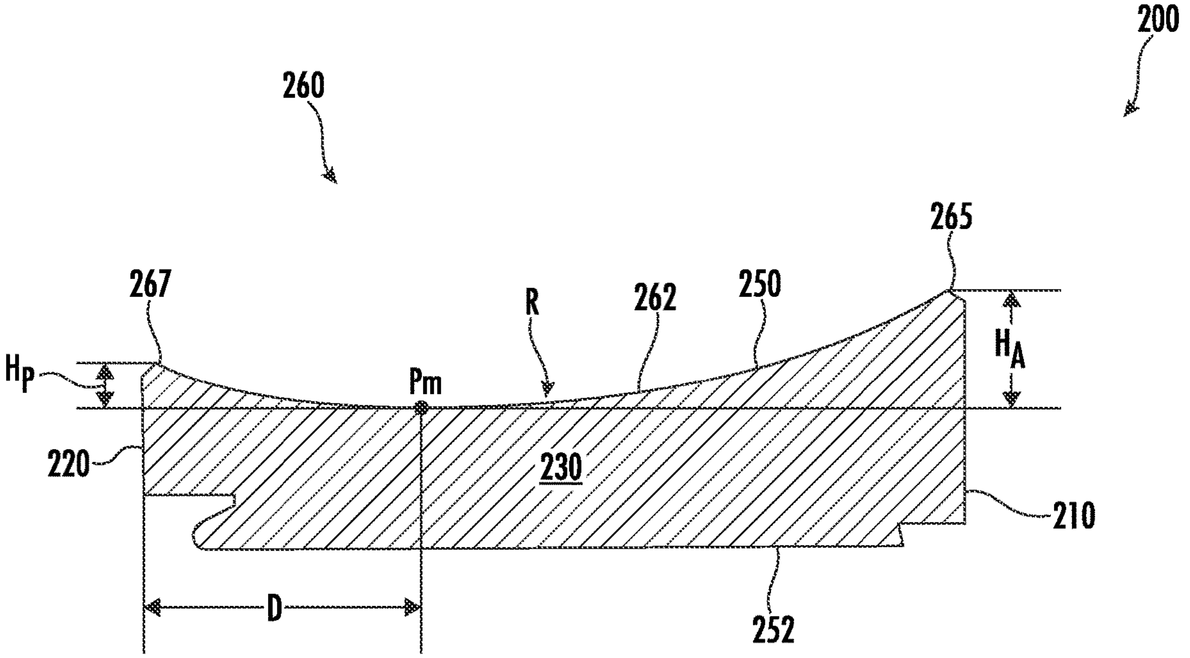
FIG. 9 is a cross-sectional view of the insert shown in FIG. 2, the cross-sectional view taken through the medial articular surface of the insert along line IX-IX in FIG. 8 (i.e., the cross-sectional view taken along a designed contact path on the medial side measuring 24 mm from a midline of the insert)

As best illustrated in FIG. 9, which illustrates a cross-sectional view of the insert 200 passing through the medial compartment 260, the cross-section taken at a distance of approximately 24 mm from a midpoint of the insert 200, the medial compartment 260 includes a generally concave top surface 262 that extends from the posterior surface 220 to the anterior surface 210 thereof. In accordance with one or more features of the present disclosure, the bottom or lowest point P of the concave top surface 262, which may also be referred to as a sulcus point $P_m$, may be positioned a distance D from the posterior surface 220 of the insert 200. As such, in accordance with one or more features of the present disclosure, the sulcus point $P_m$ of the concave top surface 262 is positioned closer to the posterior surface 220 of the insert 200 as compared to existing inserts incorporating a convex lateral articular surface without requiring the insert to extend more anteriorly.

In one example embodiment, the sulcus point $P_m$ of the concave top surface 262 may be positioned a distance D from the posterior surface 220 of the insert 200 with distance D being approximately equal to 25% to 50% percent of the overall width (e.g., anterior/posterior dimension) of the insert 200, preferably 30% to 45% percent, more preferably 35% to 40% percent. In one embodiment, the distance D may be approximately 35% to 37% of the overall width (e.g., anterior/posterior dimension) of the insert 200. In one example embodiment, the concave top surface 262 of the medial compartment 260 may have a radius of curvature R ranging between 102% to 125% of the contacting portion of the medial femoral condyle for compatible femoral components. As will be appreciated by one of ordinary skill in the art, the radius of curvature may vary depending on the size (e.g., width) of the insert.

In addition, by arranging the sulcus point $P_m$ of the concave top surface 262 closer to the posterior surface 220 than the anterior surface 210, the insert 200 is arranged and configured to provide an increased height $H_A$ at the anterior lip 265. In one example embodiment, the height $H_A$ at the anterior lip 265 as measured from the sulcus point $P_m$ of the concave top surface 262 to the tip of the anterior lip 265 measured at a cross-section representing the approximate edge of femoral contact area (e.g., a cross-section at the approximate most mesial (or nearest to midline) edge of the femoral area of contact on the insert, approximately 13.5 mm from a midline of the insert) and relative to respective sulcus of the receiving femoral condyle, may be from 6.5 mm to 10 mm. In contrast, the insert 200 may include a smaller height $H_p$ at the posterior lip 267 (e.g., the height of the lip at the posterior lip 267 is smaller than the height of the lip at the anterior lip 265). In one example embodiment, the height $H_p$ at the posterior lip 267 as measured from the sulcus point $P_m$ of the concave top surface 262 to the tip of the posterior lip 267 may be from 3 mm to 4 mm. As will be appreciated by one of ordinary skill in the art, the height $H_A$ at the anterior lip 265 and the height $H_p$ at the posterior lip 267 may vary depending on the size (e.g., A/P width) of the insert.

As will be described and illustrated in greater detail below, by incorporating a medial compartment with a concave top surface having a more posterior sulcus (e.g., the sulcus point $P_m$ (e.g., the bottom or lowest point of the concave top surface 262) is positioned closer to the posterior surface 220) and by incorporating an increased height $H_A$ for the anterior lip, the insert 200 is arranged and configured to provide improved stability for varying grades of PCL deficiencies compared to existing inserts in the marketplace that have a mid-line sulcus and lateral convexity. Thus arranged, the insert 200 is arranged and configured to be used in knee prosthesis where the patient experiences a deficient PCL function or a resected PCL.

In contrast, as previously mentioned, the lateral compartment 270 includes at least a portion of a convex surface or curve. That is, for example, as best illustrated in FIG. 10, which illustrates a cross-sectional view of the insert 200 passing through the lateral compartment 270, the cross-section taken at a distance of approximately 24 mm from the midpoint of the insert 200, the lateral compartment 270 includes a compound top surface 272 that extends from the posterior surface 220 to the anterior surface 210 thereof (e.g., the top surface 272 of the lateral compartment 270 includes a compound curve), with at least a portion of the top surface 272 having a convex surface or curve. Thus arranged, in one embodiment, the compound top surface 272 of the lateral compartment 270 may include a first posterior segment **272*a* adjacent to the posterior lip 276, a second posterior intermediate segment 272*b*, a third intermediate segment 272*c*, an optional fourth anterior intermediate segment 272*d*, and a fifth anterior segment 272*e*, although this is but one configuration and the compound top surface 272** may include more or less segments.

In one embodiment, the first posterior segment **272*a* may form a posterior (e.g., a concave) curve that begins to form a lipped area at the posterior lip 276. In use, the size of the first posterior segment 272*a* grows with larger insert sizes. The second posterior intermediate segment 272*b* and the fifth anterior segment 272*e* may each include a concave surface or curve while the third intermediate segment 272*c* includes a convex surface or curve. The optional fourth anterior intermediate segment 272*d* may include a flat surface or segment positioned between the third intermediate segment 272*c* and the fifth anterior segment 272*e*. In use, the flat surface or segment 272*d* extends posteriorly for a short distance from the fifth anterior segment 272*e* before transitioning to the third intermediate segment 272*c*. In one embodiment, the second posterior intermediate segment 272*b* may have a different radius of curvature as compared to the first posterior segment 272*a*, which may impact the location of the transition point between the first posterior segment 272*a* and the second posterior intermediate segment 272*b* thus enabling for varying the slope between the second posterior intermediate segment 272*b* and the third intermediate segment and/or increasing or decreasing the height $H_p$ at the posterior lip 276 in the lateral compartment 270**.

In one embodiment, in accordance with one or more features of the present disclosure, the sulcus point $P_L$ of the compound top surface 272 for the lateral compartment 270 occurs at the point of transition between the fifth anterior segment **272*e* and the optional fourth anterior intermediate segment 272*d* (e.g., the sulcus point $P_L$ is positioned at the point where the fifth anterior segment 272*e* meets the adjoining fourth anterior intermediate segment 272***d*). That is, the sulcus point $P_L$ of the compound top surface 272 for the lateral compartment 270 is at the posterior end of the anterior concave radius curve (e.g., anterior segment 272*e*). The sulcus point $P_L$ may be positioned a distance D from the posterior surface 220 of the insert 200. As such, in accordance with one or more features of the present disclosure, the sulcus point $P_L$ of the compound top surface 272 of the lateral compartment 270 may be positioned closer to the anterior surface 210 of the insert 200 than to the posterior surface 220. In one example embodiment, the sulcus point $P_L$ of the compound top surface 272 may be positioned a distance D from the posterior surface 220 of the insert 200 with distance D being approximately 40% to 75%, preferably 50% to 65% of the overall width (e.g., anterior/posterior dimension) of the insert 200.

Thus arranged, in accordance with one or more features of the present disclosure, the sulcus point $P_L$ of the lateral compartment 270 may be positioned closer to the anterior surface 210 of the insert 200 than the sulcus point $P_m$ of the medial compartment 260 (e.g., the sulcus point $P_m$ of the medial compartment 260 is positioned closer to the posterior surface of the insert than the sulcus point $P_L$ of the lateral compartment 270). For example, in one embodiment, the sulcus point $P_L$ of the lateral compartment 270 may be positioned more anteriorly than the sulcus point $P_m$ of the medial compartment 260 by approximately 10 to 35 percent an overall distance between the posterior and anterior surfaces.

In one example embodiment, the transition point T of the compound top surface 272 for the lateral compartment 270 occurs at the point of transition to the posterior convexity (e.g., point of transition between the optional fourth anterior intermediate segment 272*d* and the third intermediate segment 272*c* (e.g., the transition point T is positioned at the point where the fourth anterior intermediate segment 272*d* meets the adjoining third intermediate segment 272*c*)). As such, the transition point T is defined as the anterior start of the convex radius of the third intermediate segment 272*c* (e.g., at the posterior end of the fourth anterior intermediate segment 272*d*) while the sulcus point $P_L$ is defined at the anterior end of the fourth anterior intermediate segment 272*d*. In use, in one embodiment, since the sulcus point $P_L$ and the transition point T may be connected by a flat surface (e.g., optional fourth anterior intermediate segment 272*d*), they may be positioned at the same height from the bottom surface of the insert. Alternatively, however, if the compound top surface 272 for the lateral compartment 270 is devoid of the optional fourth anterior intermediate segment 272*d*, the sulcus point $P_L$ and the transition point T may also coincide along the A/P width. As illustrated, in one embodiment, the transition point T may be positioned a distance T from the posterior surface 220 of the insert 200 with distance T being approximately 30% to 60%, preferably 35% to 55%, more preferably 40% to 50% of the overall width (e.g., anterior/posterior dimension) of the insert.

As used herein, by individually defining the sulcus point $P_L$ and the transition point T, it enables alternate embodiments where the top surface 272 includes additional segments or lengths of either a flat, another concave radiused portion that transitions to a flat or on to a convex curve, or a transition to a convex radius without any intermediate portion.

Thus arranged, the insert 200 is arranged and configured to provide a height $H_A$ at the anterior lip 275 in the lateral compartment 270. In one example embodiment, the height $H_A$ at the anterior lip 275 in the lateral compartment 270 as measured from the sulcus point $P_L$ to the tip of the anterior lip 275 measured at a cross-section representing the approximate edge of femoral contact area (e.g., a cross-section at the approximate most mesial (or nearest to midline) edge of the femoral area of contact on the insert, approximately 13.5 mm from midline) and relative to respective sulcus of the receiving femoral condyle, may be from 2.5 mm to 4.5 mm. In contrast, the insert 200 may include a height $H_p$ at the posterior lip 276 in the lateral compartment 270. In one example embodiment, the height $H_p$ at the posterior lip 276 may be from 0.5 mm to 1.5 mm. As will be appreciated by one of ordinary skill in the art, the height $H_p$ at the posterior lip 276 may vary depending on the size (e.g., A/P width) of the insert. For example, the depth or height of the posterior lip 276 is greatest on the smallest insert sizes at around 1.5 mm below the sulcus point $P_L$. In use, as the size of the inserts grow, the posterior lip becomes more prominent, rising a little higher due to the additional first posterior segment 272*a*. For the largest sized inserts, the depth (or height of the posterior lip) is approximately 0.5 mm below the sulcus point $P_L$.

In one example embodiment, the anterior most segment or portion (e.g., the fifth anterior segment 272*e* (FIG. 10)) of the concave top surface 272 of the lateral compartment 270 may have a radius of curvature R ranging between 155% to 225% of the radius of the contacting portion of the lateral femoral condyle for compatible femoral components. In use, the radius of curvature for the lateral side is arranged and configured to facilitate motion (e.g., screw home in extension) since the lateral compartment is more relaxed, which is in contrast to the radius of curvature of the medial compartment, which is arranged and configured to constrain motion. As will be appreciated by one of ordinary skill in the art, the radius of curvature may vary depending on the size (e.g., width) of the insert.

In accordance with one or more features of the present disclosure, an improved insert 200 for use in a knee prosthesis such as, for example, knee prosthesis 100, is provided. For example, by incorporating a medial compartment 260 with a concave top surface 262 and a lateral compartment 270 with a compound top surface 272 including at least a portion of a convex surface, an articular insert 200 is provided that is arranged and configured to facilitate performing a cruciate-retaining or a cruciate-substituting TKA procedure with an option for better adapting to the needs of the patient and the varying soft tissue conditions which can impact knee replacement function and long-term clinical success.

In accordance with one or more features of the present disclosure, by incorporating a medial compartment 260 with a concave top surface 262 having a more posterior sulcus and increased anterior lip, the insert 200 provides improved stability for varying grades of PCL deficiencies compared to existing inserts in the marketplace that have a mid-line sulcus and lateral convexity (as evidence by FIGS. 13, 14, 18, and 19).

Conversely, in accordance with one or more features of the present disclosure, by incorporating a medial compartment 260 with a concave top surface 262 and a lateral compartment 270 with at least a partial convexity, the insert 200 is arranged and configured to promote improved lateral posterior translation compared to existing inserts in the marketplace that have a concave or flat lateral articulation (FIGS. 15, 16, 17, 20, 21, and 22).

Moreover, in use, the insert 200 is arranged and configured to be implanted in procedures where the patient's PCL is retained. Referring to FIGS. 13-17, the insert 200 is utilized within a knee prosthesis where the patient's PCL is retained. As evidence by the data in FIGS. 13-17, the insert 200 performs similarly to existing Insert 1. During use, utilizing the insert 200 with the patient's PCL retained, flexion is maintained and comparable amounts of medial translation (as provided for in FIGS. 13 and 14), lateral translation (as provided for in FIGS. 15 and 16) and internal/external rotation (as provided for in FIG. 17) can be achieved. Posterior femoral rollback (e.g., translation) (FIGS. 15 and 16) and internal/external rotation (FIG. 17) is improved over more constraining designs (existing Insert 2), which also provides additional A/P constraint in the instance where the PCL is retained and integrity of the ligament is not pristine initially or becomes increasingly deficient post-operatively.

Conversely, FIGS. 18-22 demonstrate that the insert 200 can also be utilized in procedures where the patient's PCL is sacrificed. Referring to FIGS. 18-22, the insert 200 is utilized within a knee prosthesis where the patient's PCL is sacrificed. As evidence by the data in FIGS. 18-22, the insert 200 performs similarly to existing Insert 2 with some improvements. Translation within the medial compartment is similar to the more constraining design (existing Insert 2) with the advantage of the femoral dwell point being more anterior in extension (as provided for in FIGS. 18 and 19). In addition, these figures demonstrate improved stability over standard CR insert designs for PCL sacrificed or severely deficient PCL conditions. Laterally, the insert 200 promotes improved posterior translation (as provided for in FIGS. 20 and 21) and internal/external rotation (as provided for in FIG. 22) of the femur in deeper flexion over the more constraining Insert 2.

Referring to FIGS. 13-22, test data comparing the insert 200 in accordance with one or more features of the present disclosure (e.g., an insert 200 incorporating a medial compartment 260 with a concave top surface 262 having a more posterior sulcus and increased anterior lip and a lateral compartment 270 having at least a partial convexity) versus existing inserts in the marketplace and/or a normal knee is illustrated. As illustrated, insert 200 is compared to an existing insert (Insert 1) which incorporates a medial compartment having a concave top surface that includes a mid-line sulcus and lateral convexity and to an existing insert (Insert 2) which incorporates a concave top surface in both the medial and lateral compartments.

Figure 13:
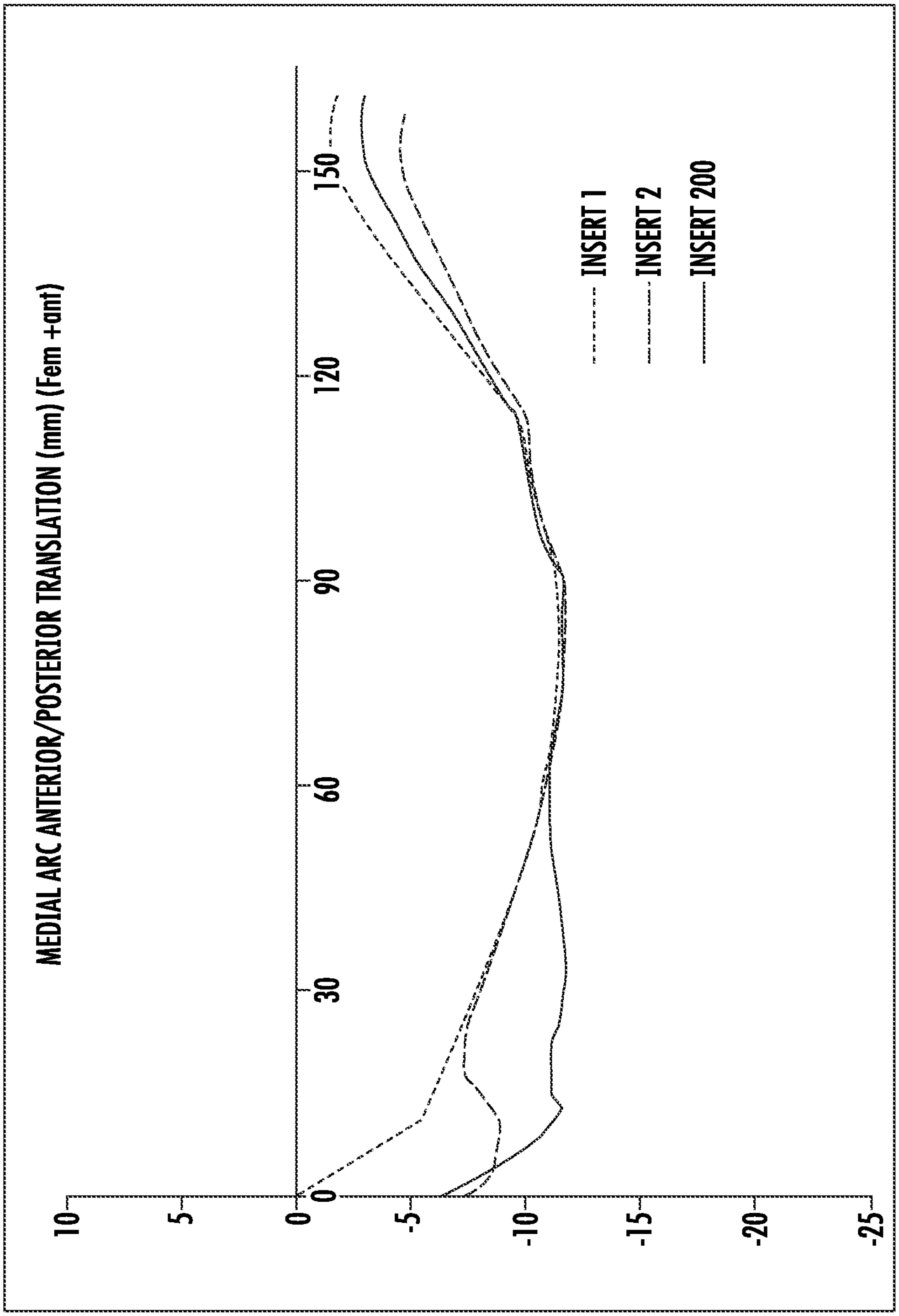
FIGS. 13-22 illustrate various test data comparing the insert shown in FIG. 2 against the known existing inserts (e.g., existing Insert 1 and existing Insert 2).

Referring to FIG. 13 illustrates the tibiofemoral kinematics describing anterior/posterior translation within the medial compartment of insert 200 compared to existing Insert 1 and existing Insert 2 when used in a PCL-retained condition.

Figure 14:
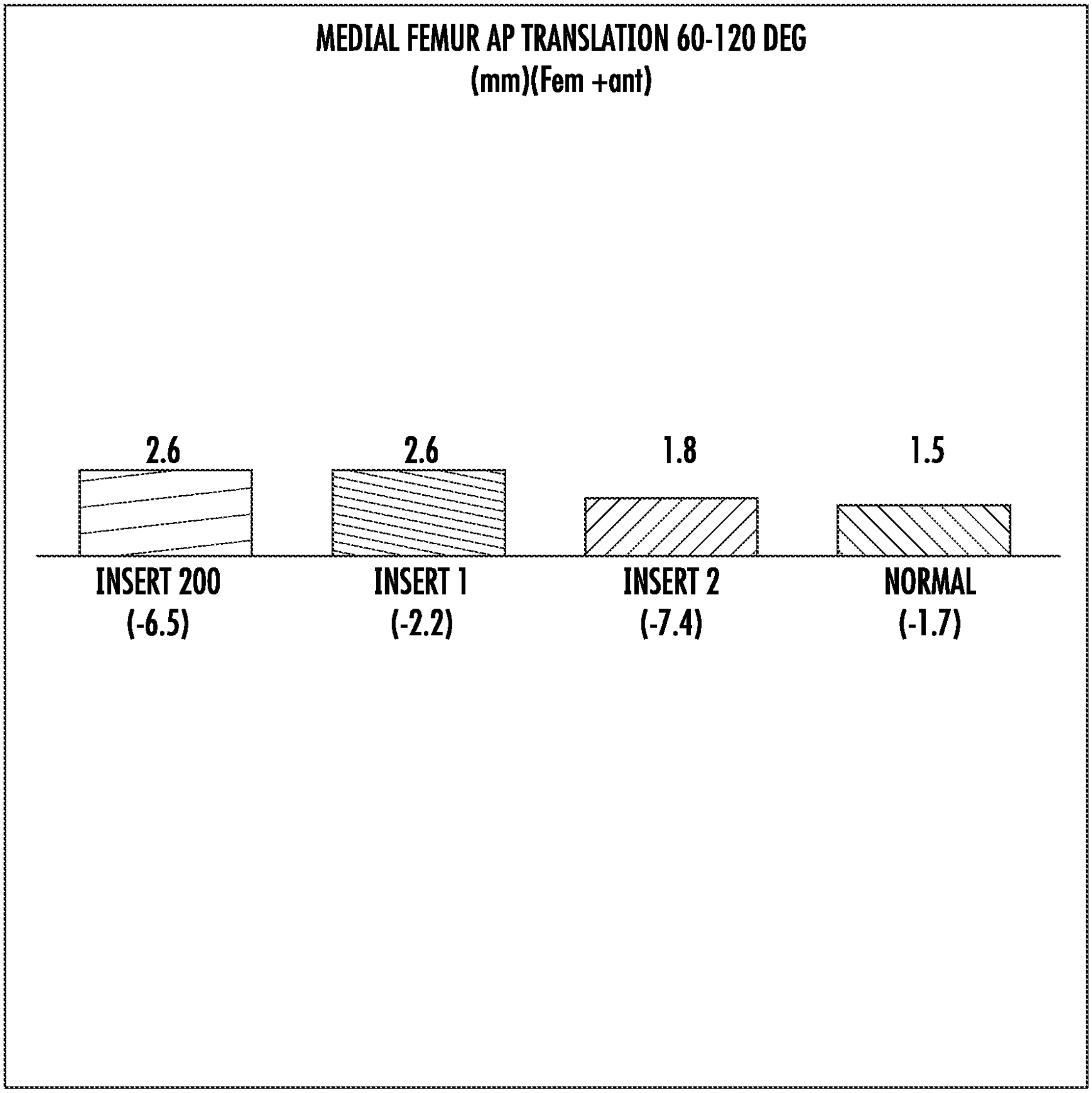

Referring to FIG. 14 illustrates translation of the medial femoral condylar arc with respect to the tibia during flexion of the knee between 60 degrees and 120 degrees of insert 200 compared to existing Insert 1 and existing Insert 2 when used in a PCL-retained condition and compared to a normal knee. Values within parentheses describe the location of the medial condylar arc low point relative to the midline of the tibia at full extension.

Figure 15:
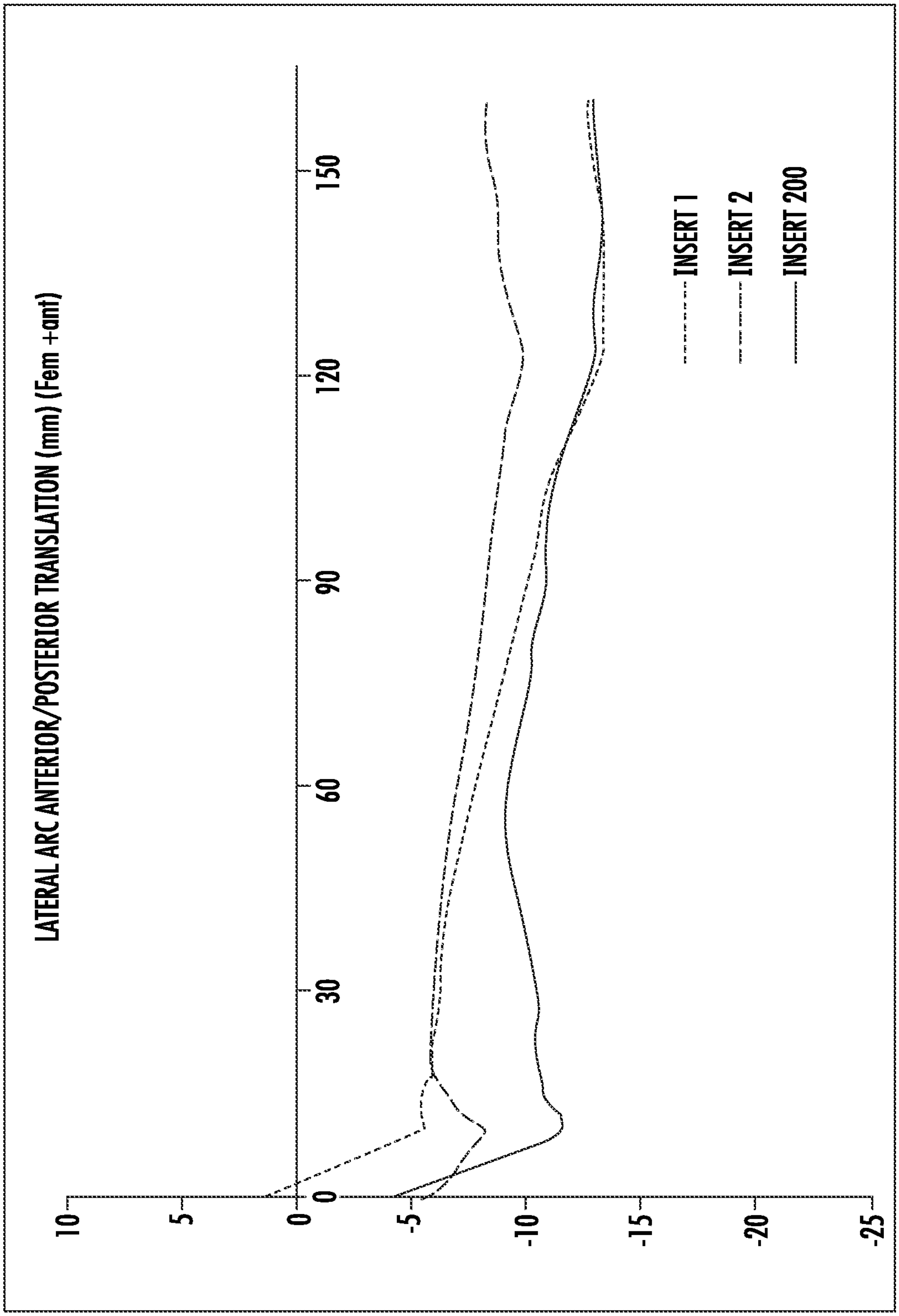

Referring to FIG. 15 illustrates the tibiofemoral kinematics describing anterior/posterior translation within the lateral compartment of insert 200 compared to existing Insert 1 and existing Insert 2 in the marketplace when used in a PCL-retained condition.

Figure 16:
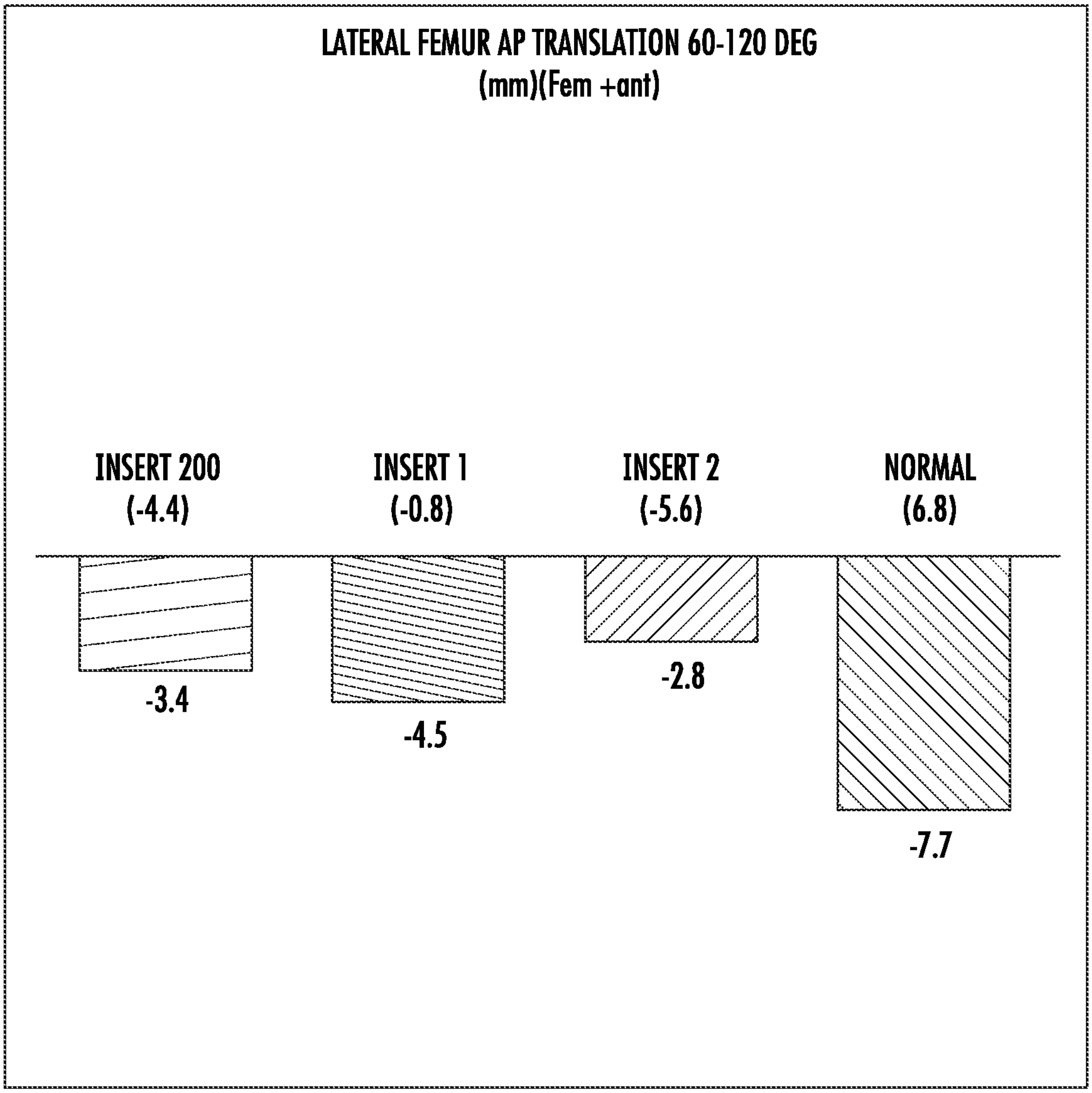

Referring to FIG. 16 illustrates translation of the lateral femoral condylar arc with respect to the tibia during flexion of the knee between 60 degrees and 120 degrees of insert 200 compared to existing Insert 1 and existing Insert 2 when used in a PCL-retained condition and a normal knee. Values within parentheses describe the location of the lateral condylar arc low point relative to the midline of the tibia at full extension.

Figure 17:
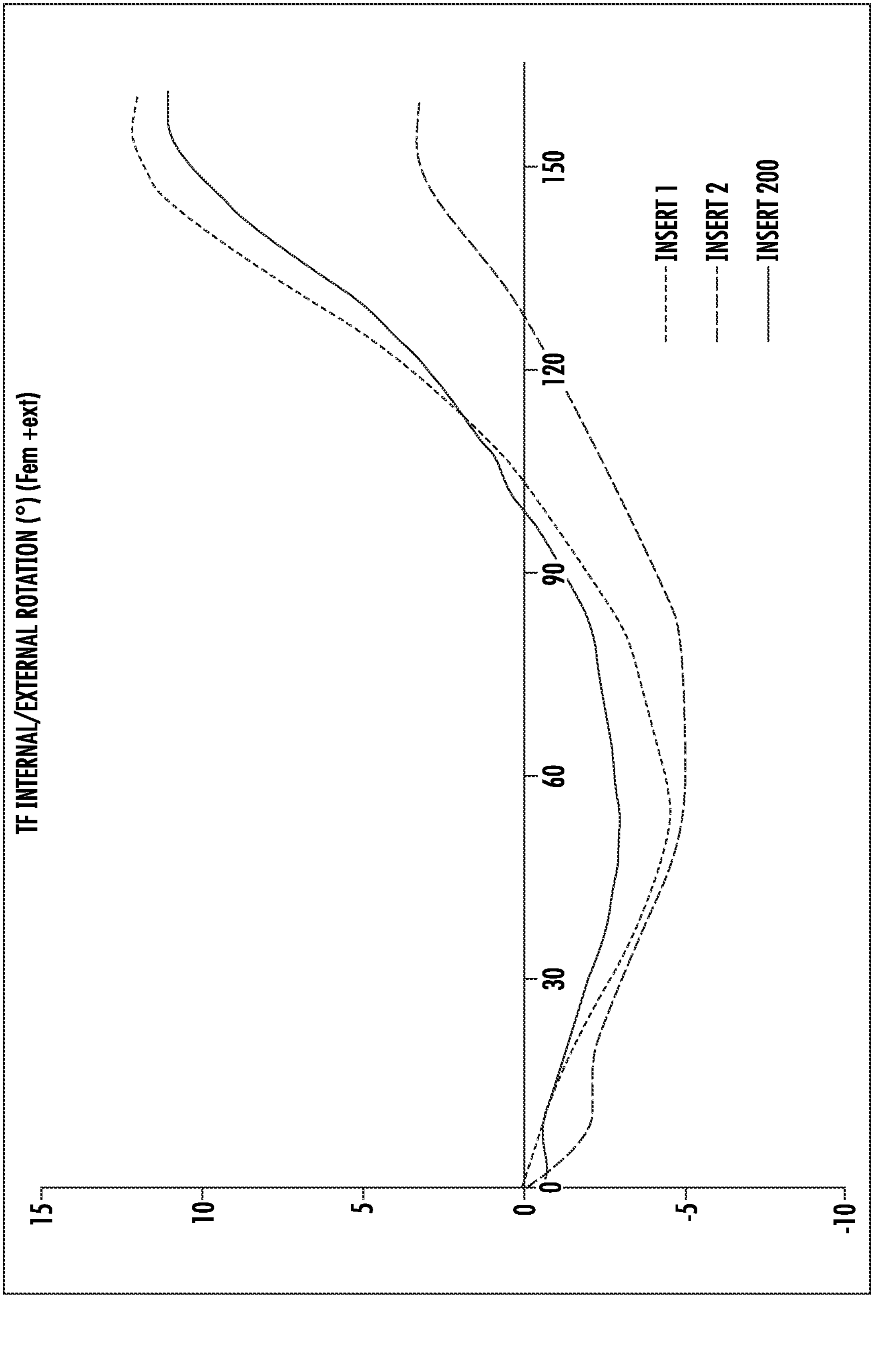

Referring to FIG. 17 illustrates the tibiofemoral kinematics describing internal/external rotation of insert 200 compared to existing Insert 1 and existing Insert 2 when used in a PCL-retained condition.

Figure 18:
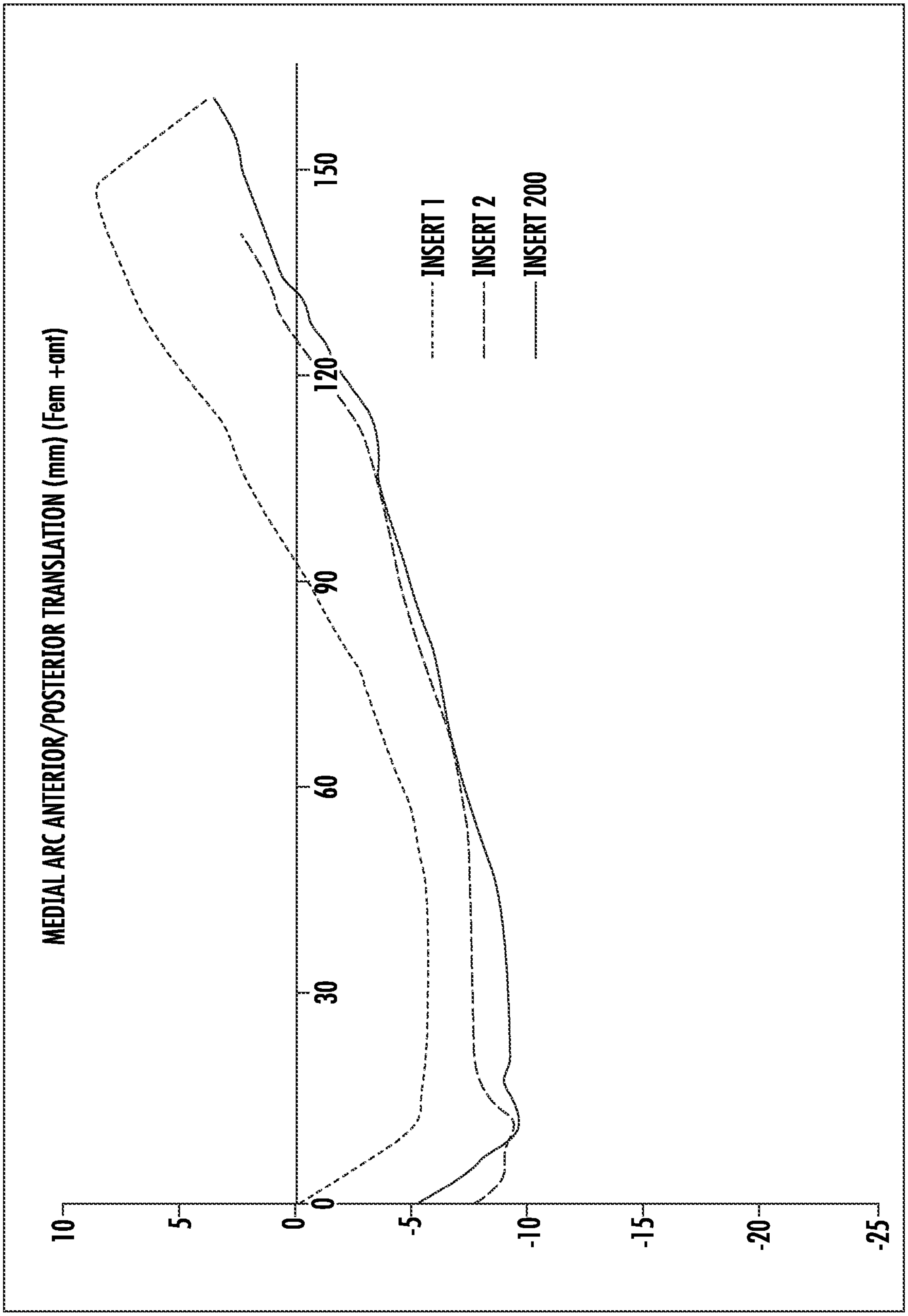

Referring to FIG. 18 illustrates the tibiofemoral kinematics describing anterior/posterior translation within the medial compartment of insert 200 compared to existing Insert 1 and existing Insert 2 when used in a PCL-sacrificed condition.

Figure 19:
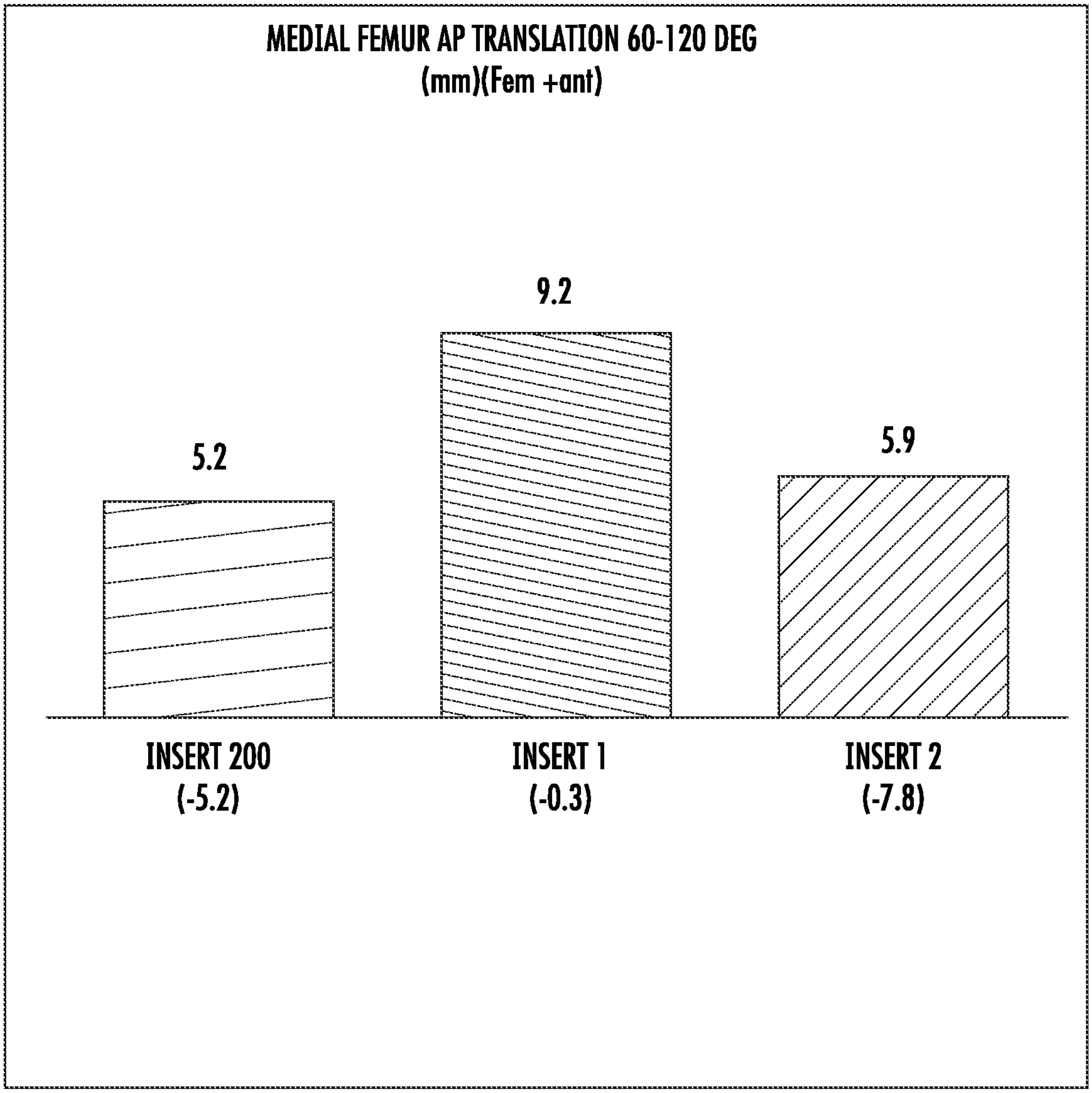

Referring to FIG. 19 illustrates translation of the medial femoral condylar arc with respect to the tibia during flexion of the knee between 60 degrees and 120 degrees of insert 200 compared to existing Insert 1 and existing Insert 2 when used in a PCL-sacrificed condition. Values within parentheses describe the location of the medial condylar arc low point relative to the midline of the tibia at full extension.

Figure 20:
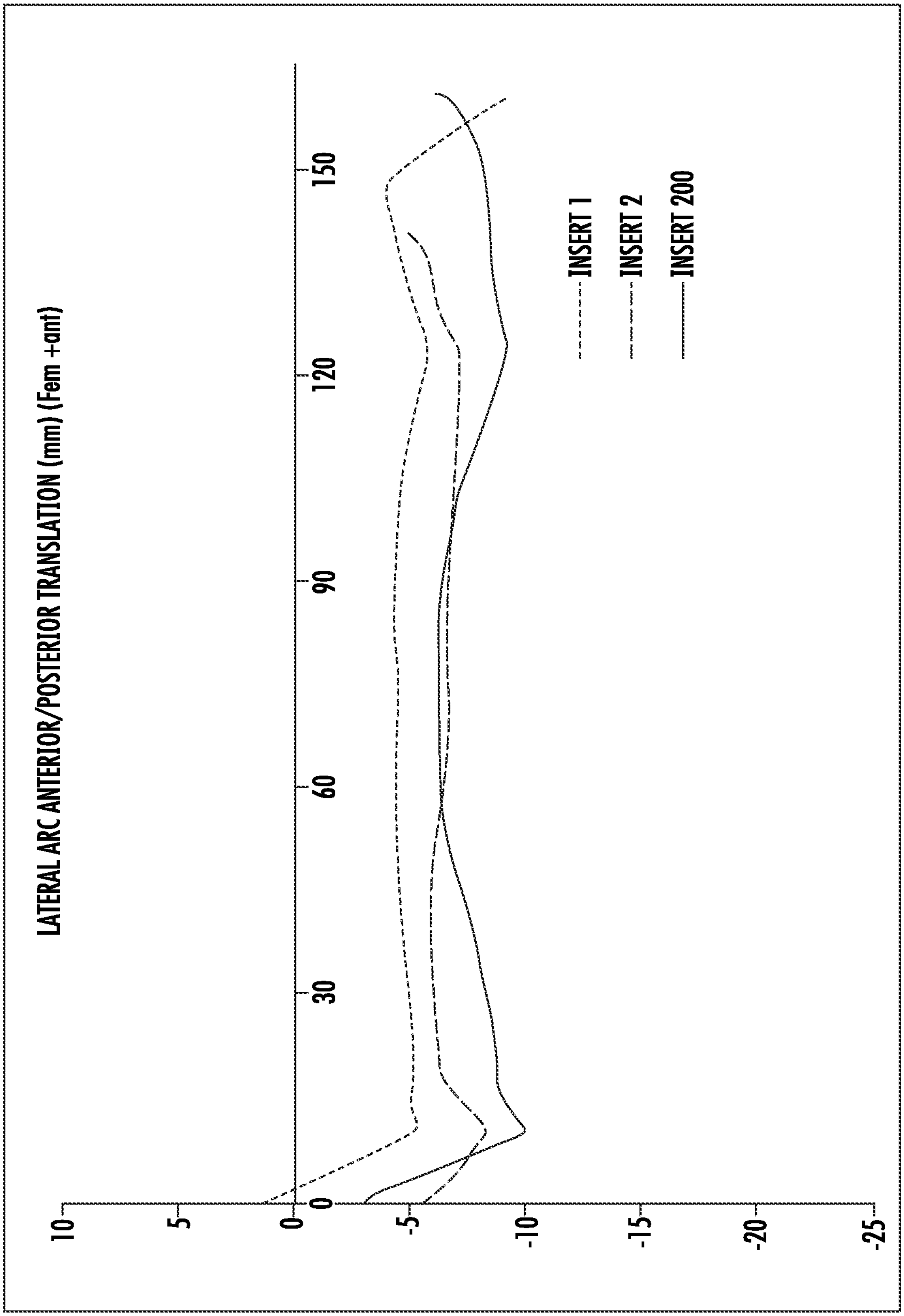

Referring to FIG. 20 illustrates the tibiofemoral kinematics describing anterior/posterior translation within the lateral compartment of insert 200 compared to existing Insert 1 and existing Insert 2 when used in a PCL-sacrificed condition.

Figure 21:
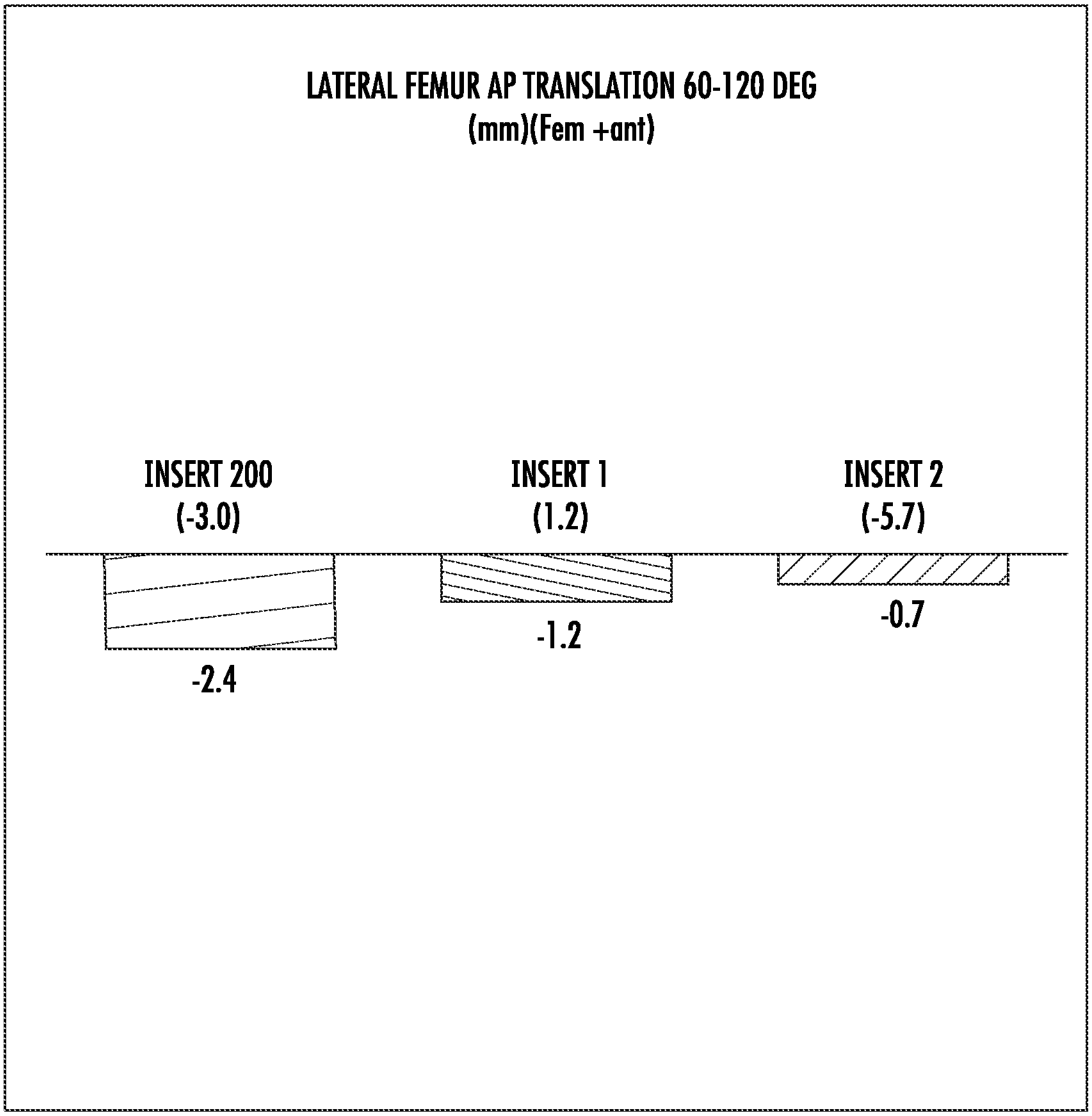

Referring to FIG. 21 illustrates translation of the lateral femoral condylar arc with respect to the tibia during flexion of the knee between 60 degrees and 120 degrees of insert 200 compared to existing Insert 1 and existing Insert 2 when used in a PCL-sacrificed condition. Values within parentheses describe the location of the lateral condylar arc low point relative to the midline of the tibia at full extension.

Figure 22:
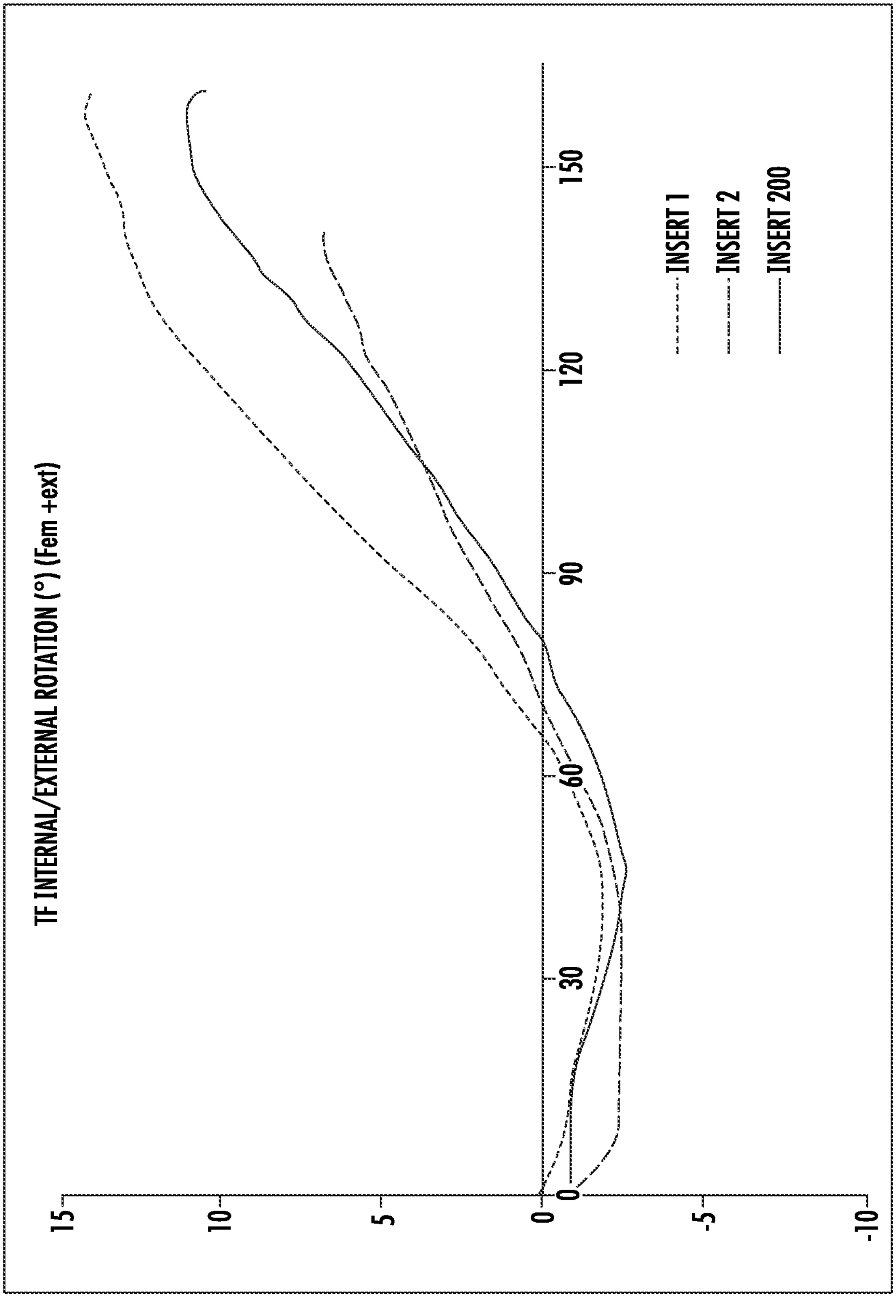

Referring to FIG. 22 illustrates the tibiofemoral kinematics describing internal/external rotation of insert 200 compared to existing Insert 1 and existing Insert 2 when used in a PCL-sacrificed condition.

In use, as previously mentioned, the insert 200 can be used in conjunction with any suitable knee prosthesis (e.g., femoral and tibial components) now known or hereafter developed. In addition, the insert 200 can be manufactured from any suitable bio-compatible material now known or hereafter developed used to manufacture orthopedic inserts including, for example, a plastic or polymeric material such as, for example, an ultra-high molecular weight polyethylene. In addition, the inserts 200 may be constructed from any suitable manner now know or hereafter developed. For example, the insert 200 may be machined, molded, or otherwise constructed as a one-piece, integral unit out of medical grade, physiologically acceptable plastic such as ultra-high molecular weight polyethylene or the like, in various sizes to fit a range of typical patients, or may be custom-designed for a specific patient based on data provided by a surgeon after physical and radiographic examination of the specific patient. The material can be treated, for example, by radiation, chemistry, or other technology to alter its wear properties and/or strength or hardness. Portions of various surfaces of inserts can be treated with radiation, chemicals or other substances or techniques to enhance wear resistance properties; they can also be subjected to suitable surface treatments for such purposes and others.

In use, the insert 200 may be provided individually, as part of a knee prosthesis or as part of a kit including various sized inserts, tibial components, and/or femoral components. Alternatively, a patient-matched knee prosthesis may be provided with certain geometries and/or other features of the implant customized for a particular patient's anatomy.

Terms such as top, bottom, superior, inferior, medial, lateral, anterior, posterior, proximal, distal, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited.

The phrases "at least one", "one or more", and "and/or", as used herein, are open-ended expressions that are both conjunctive and disjunctive in operation. The terms "a" (or "an"), "one or more" and "at least one" can be used interchangeably herein. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. A knee prosthesis comprising:

a femoral component including a medial condylar surface, a lateral condylar surface, and an articular surface;

a tibial component including a load bearing component; and an insert positioned between the articular surface and the load bearing component, the insert including an anterior surface, a posterior surface, a medial surface, a lateral surface, a medial component, and a lateral component, wherein:

the medial component includes a top surface arranged and configured to contact the medial condylar surface, the top surface of the medial component including a medial sulcus point; and the lateral component includes a top surface arranged and configured to contact the lateral condylar surface, the top surface of the lateral component including a lateral sulcus point;

wherein:

the medial sulcus point is positioned closer to the posterior surface than to the anterior surface;

the medial sulcus point is positioned closer to the posterior surface of the insert than the lateral sulcus point;

the lateral sulcus point is positioned closer to the anterior surface than to the posterior surface; and the lateral sulcus point is positioned more anteriorly than the medial sulcus point by approximately 10 to 35 percent an overall distance between the posterior and anterior surfaces;

wherein the top surface of the medial component includes a concave surface that extends completely from the posterior surface to the anterior surface, and the top surface of the lateral component includes a compound curve having at least a segment thereof including a convex surface;

wherein the compound curve of the top surface of the lateral compartment includes an anterior concave segment and a posterior concave segment;

wherein the medial component includes an anterior lip having a height HA as measured from the medial sulcus point to a tip of the anterior lip, and a posterior lip having a height Hp as measured from the medial sulcus point to a tip of the posterior lip, where height HA is greater than height Hp.

2. The knee prosthesis of claim 1, wherein the lateral sulcus point is positioned a distance D from the posterior surface with distance D being approximately 50 to 65 percent of an overall distance between the posterior and anterior surfaces.

3. The knee prosthesis of claim 2, wherein the medial sulcus point is positioned a distance D from the posterior surface with distance D being approximately 30 to 45 percent of the overall distance between the posterior and anterior surfaces.

4. The knee prosthesis of claim 1, wherein the medial sulcus point is positioned a distance D from the posterior surface with distance D being approximately 35 to 40 percent of the overall distance between the posterior and anterior surfaces.

5. The knee prosthesis of claim 1, wherein the height HA at the anterior lip is between 6.5 mm and 10 mm and the height Hp at the posterior lip is between 3 mm and 4 mm.

6. The knee prosthesis of claim 1, wherein the posterior concave segment is positioned between the posterior surface and the convex segment.

7. The knee prosthesis of claim 6, wherein the compound curve of the top surface of the lateral component includes a posterior concave intermediate segment positioned between the posterior concave segment and the convex segment.

8. The knee prosthesis of claim 6, wherein the compound curve of the top surface of the lateral component includes a flat segment positioned between the anterior concave segment and the convex segment.

9. The knee prosthesis of claim 8, wherein the lateral sulcus point is positioned at a transition between the anterior concave segment and the flat segment.

10. The knee prosthesis of claim 1, wherein the compound curve of the top surface of the lateral component includes a transition point defined at an anterior end of the convex segment, the transition point being positioned a distance T from the posterior surface with distance T being approximately 40% to 50% an overall distance between the posterior and anterior surfaces.

* * * * *